US 6,889,082 B2

(12) United States Patent
Bolling et al.

(10) Patent No.: US 6,889,082 B2
(45) Date of Patent: May 3, 2005

(54) IMPLANTABLE HEART ASSIST SYSTEM AND METHOD OF APPLYING SAME

(75) Inventors: Steven F. Bolling, Ann Arbor, MI (US); Anthony Viole, Foothill Ranch, CA (US); Shawn O'Leary, Mission Viejo, CA (US)

(73) Assignee: Orqis Medical Corporation, Lake Forest, CA (US)

( * ) Notice: Subject to any disclaimer, the term of this patent is extended or adjusted under 35 U.S.C. 154(b) by 365 days.

(21) Appl. No.: 10/289,467

(22) Filed: Nov. 6, 2002

(65) Prior Publication Data
US 2003/0069468 A1 Apr. 10, 2003

Related U.S. Application Data

(63) Continuation-in-part of application No. 10/171,023, filed on Jun. 11, 2002, now Pat. No. 6,685,621, which is a continuation-in-part of application No. 10/078,260, filed on Feb. 15, 2002, now Pat. No. 6,610,004, which is a continuation-in-part of application No. 09/552,979, filed on Apr. 21, 2000, now Pat. No. 6,390,969, which is a continuation-in-part of application No. 09/470,841, filed on Dec. 23, 1999, now Pat. No. 6,387,037, which is a continuation-in-part of application No. 09/289,231, filed on Apr. 9, 1999, now Pat. No. 6,428,464, which is a continuation-in-part of application No. 09/166,005, filed on Oct. 2, 1998, now Pat. No. 6,200,260

(60) Provisional application No. 60/061,434, filed on Oct. 9, 1997.

(51) Int. Cl.[7] .............................................. A61M 1/10
(52) U.S. Cl. ........................................... 607/16; 607/17
(58) Field of Search .................... 600/16, 17; 623/3.11, 623/3.13, 3.16–3.17

(56) References Cited

U.S. PATENT DOCUMENTS

| 2,876,769 A | 3/1959 | Cordova ..................... 422/4.5 |
| 2,935,068 A | 5/1960 | Donaldson .................. 604/17.5 |
| 3,017,885 A | 1/1962 | Robicsek ..................... 604/6.1 |
| 3,592,184 A | 7/1971 | Watkins et al. ............. 604/192 |
| 3,692,018 A | 9/1972 | Goetz et al. .................. 600/18 |
| 3,835,864 A | 9/1974 | Rasor et al. .................. 607/36 |
| 3,885,251 A | 5/1975 | Padrosa ..................... 623/3.17 |
| 3,938,530 A | 2/1976 | Santomieri .................. 604/105 |
| 3,939,820 A | 2/1976 | Grayzel ....................... 600/18 |

(Continued)

FOREIGN PATENT DOCUMENTS

| EP | 0232074 | 1/1987 | .......... A61M/25/00 |
| EP | 0 411 605 A1 | 1/1990 | .......... A61M/25/00 |
| EP | 0 405 749 A1 | 5/1990 | ............ A61M/1/10 |

(Continued)

OTHER PUBLICATIONS

Jama, Jan. 8, 1968, vol. 203. No. 2, Initial Clinical Experience with Intra-aortic Balloon Pumping ing Cardiogenic Shock, PP 113–118.

(Continued)

Primary Examiner—Carl Layno
(74) Attorney, Agent, or Firm—Knobbe, Martens, Olson & Bear LLP

(57) ABSTRACT

An extracardiac pumping for supplementing the circulation of blood, including the cardiac output, in a patient without any component thereof being connected to the patient's heart, and methods of using same. One embodiment provides a vascular graft that has a first end that is sized and configured to couple to a non-primary blood vessel and a second end that is fluidly coupled to a pump to conduct blood between the pump and the non-primary blood vessel. An outflow conduit is also provided that has a first end sized and configured to be positioned within the same or different blood vessel, whether primary or non-primary, through the vascular graft. The outflow conduit is fluidly coupled to the pump to conduct blood between the pump and the patient. The vascular graft may be connected to the blood vessel subcutaneously to permit application of the extracardiac pumping system in a minimally-invasive procedure.

14 Claims, 15 Drawing Sheets

U.S. PATENT DOCUMENTS

| | | |
|---|---|---|
| 3,964,479 A | 6/1976 | Boag et al. ............... 604/123 |
| 4,004,299 A | 1/1977 | Runge ..................... 623/3.18 |
| 4,034,742 A | 7/1977 | Thoma ....................... 600/17 |
| 4,047,849 A | 9/1977 | Clay ......................... 417/384 |
| 4,051,840 A | 10/1977 | Kantrowitz et al. .......... 600/18 |
| 4,077,394 A | 3/1978 | McCurdy ..................... 600/18 |
| 4,080,958 A | 3/1978 | Bregman et al. ............. 600/16 |
| 4,135,496 A | 1/1979 | Chazov et al. ................ 600/17 |
| 4,143,616 A | 3/1979 | Bible ........................ 116/266 |
| 4,154,227 A | 5/1979 | Krause et al. ................ 600/18 |
| 4,167,046 A | 9/1979 | Portner et al. .............. 623/317 |
| 4,240,409 A | 12/1980 | Robinson et al. ............ 600/16 |
| 4,302,854 A | 12/1981 | Runge ..................... 623/3.11 |
| 4,384,829 A | 5/1983 | Conely et al. .............. 417/412 |
| 4,407,271 A | 10/1983 | Schiff ......................... 600/17 |
| 4,457,673 A | 7/1984 | Conley et al. .............. 417/412 |
| 4,459,977 A | 7/1984 | Pizon et al. ................. 600/17 |
| 4,522,195 A | 6/1985 | Schiff ......................... 600/18 |
| 4,546,759 A | 10/1985 | Solar ......................... 600/18 |
| 4,552,522 A | 11/1985 | Polaschegg et al. ........ 425/182 |
| 4,569,332 A | 2/1986 | Schiff et al. .................. 600/18 |
| 4,573,997 A | 3/1986 | Wisman et al. ............ 623/3.16 |
| 4,611,578 A | 9/1986 | Heimes ....................... 600/19 |
| 4,625,712 A | 12/1986 | Wampler ................... 600/16 |
| 4,666,443 A | 5/1987 | Portner ..................... 623/3.12 |
| 4,685,446 A | 8/1987 | Choy ......................... 600/18 |
| 4,688,998 A | 8/1987 | Olsen et al. ................ 417/356 |
| 4,690,134 A | 9/1987 | Snyders ..................... 601/153 |
| 4,697,574 A | 10/1987 | Karcher et al. .............. 600/17 |
| 4,719,921 A | 1/1988 | Chirife ....................... 607/23 |
| 4,756,302 A | 7/1988 | Portner et al. .............. 600/17 |
| 4,759,760 A | 7/1988 | Snapp, Jr. .................. 623/3.12 |
| 4,771,765 A | 9/1988 | Choy et al. ................. 600/18 |
| 4,822,357 A | 4/1989 | Forster et al. ............. 623/3.18 |
| 4,838,889 A | 6/1989 | Kolff ......................... 623/3.21 |
| 4,861,330 A | 8/1989 | Voss ........................... 600/18 |
| 4,872,874 A | 10/1989 | Taherin ....................... 128/898 |
| 4,883,462 A | 11/1989 | Williamson et al. ........ 604/540 |
| 4,895,150 A | 1/1990 | Isaacson et al. ........... 623/3.27 |
| 4,902,272 A | 2/1990 | Milder et al. ................. 600/18 |
| 4,902,273 A | 2/1990 | Choy et al. ................. 600/18 |
| 4,906,229 A | 3/1990 | Wampler ..................... 600/16 |
| 4,908,012 A | 3/1990 | Moise et al. ................. 600/16 |
| 4,927,407 A | 5/1990 | Dorman ........................ 600/16 |
| 4,957,504 A | 9/1990 | Chardack .................. 623/3.14 |
| 4,968,293 A | 11/1990 | Nelson ......................... 600/16 |
| 4,985,014 A * | 1/1991 | Orejola ......................... 600/16 |
| 4,994,078 A | 2/1991 | Jarvik ....................... 623/3.14 |
| 4,995,856 A | 2/1991 | Heindl et al. ................ 604/8 |
| 4,995,857 A | 2/1991 | Arnold ........................ 600/16 |
| 5,020,516 A | 6/1991 | Biondi et al. ............... 601/44 |
| 5,059,167 A | 10/1991 | Lundquist et al. ........... 600/17 |
| 5,069,662 A | 12/1991 | Bodden .................... 604/5.01 |
| 5,089,017 A | 2/1992 | Young et al. .............. 623/3.11 |
| 5,092,844 A | 3/1992 | Schwartz et al. ........... 604/151 |
| 5,098,370 A | 3/1992 | Rahat et al. .................. 600/16 |
| 5,116,564 A | 5/1992 | Jansen et al. ............... 264/255 |
| 5,129,878 A | 7/1992 | Takano et al. ................ 600/16 |
| 5,131,905 A | 7/1992 | Grooters ..................... 600/16 |
| 5,133,744 A | 7/1992 | Ramos Martinez ........ 623/3.21 |
| 5,147,281 A | 9/1992 | Thornton et al. ............. 600/16 |
| 5,147,388 A | 9/1992 | Yamazaki .................. 623/3.13 |
| 5,169,378 A | 12/1992 | Figuera ....................... 600/16 |
| 5,169,379 A | 12/1992 | Freed et al. ................. 600/16 |
| 5,171,207 A | 12/1992 | Whalen ....................... 600/16 |
| 5,176,619 A | 1/1993 | Segalowitz ................. 600/18 |
| 5,211,659 A | 5/1993 | Strimling et al. .......... 623/3.17 |
| 5,263,978 A | 11/1993 | Kaufmann et al. ........ 623/3.17 |
| 5,267,940 A | 12/1993 | Moulder ..................... 600/16 |
| 5,273,518 A | 12/1993 | Lee et al. ..................... 600/16 |
| 5,290,227 A | 3/1994 | Pasque ........................ 600/16 |
| 5,300,113 A | 4/1994 | Arpesella et al. .......... 623/3.21 |
| 5,332,403 A | 7/1994 | Kolff ......................... 623/3.21 |
| 5,346,458 A | 9/1994 | Affeld ......................... 600/16 |
| 5,352,180 A | 10/1994 | Candelon et al. ............ 600/17 |
| 5,374,239 A | 12/1994 | Mischenko .................... 604/8 |
| 5,376,113 A | 12/1994 | Jansen et al. .............. 623/2.19 |
| 5,413,549 A | 5/1995 | Leschinsky .................. 600/18 |
| 5,429,584 A | 7/1995 | Chiu ........................... 600/18 |
| 5,433,731 A | 7/1995 | Hoegnelid et al. ............. 607/5 |
| 5,437,601 A | 8/1995 | Runge ......................... 600/16 |
| 5,453,076 A | 9/1995 | Kiyota et al. ................. 600/18 |
| 5,503,615 A | 4/1996 | Goldstein .................... 600/16 |
| 5,511,958 A | 4/1996 | Chen et al. ................. 417/412 |
| 5,514,073 A | 5/1996 | Miyata et al. ................ 600/18 |
| 5,533,958 A | 7/1996 | Wilk ........................... 600/18 |
| 5,562,595 A | 10/1996 | Neisz .......................... 600/16 |
| 5,584,804 A | 12/1996 | Klatz et al. ................... 604/24 |
| 5,746,575 A | 5/1998 | Westphal et al. ........... 415/206 |
| 5,749,855 A | 5/1998 | Reitan ....................... 604/151 |
| 5,824,070 A | 10/1998 | Jarvik ....................... 623/3.13 |
| 5,851,174 A | 12/1998 | Jarvik et al. ................. 600/16 |
| 5,941,813 A | 8/1999 | Sievers et al. ............... 600/16 |
| 6,167,765 B1 * | 1/2001 | Weitzel .................... 73/861.18 |
| 6,200,260 B1 | 3/2001 | Bolling ....................... 600/16 |
| 6,299,575 B1 | 10/2001 | Bolling ....................... 600/16 |
| 6,387,037 B1 | 5/2002 | Bolling et al. ............... 600/16 |
| 6,390,969 B1 | 5/2002 | Bolling et al. ............... 600/16 |
| 6,428,464 B1 | 8/2002 | Bolling ....................... 600/16 |
| 6,488,662 B2 | 12/2002 | Sirimanne ............. 604/164.01 |
| 6,610,004 B2 | 8/2003 | Viole et al. .................. 600/16 |
| 6,685,621 B2 | 2/2004 | Bolling et al. ............... 600/16 |
| 2002/0111577 A1 | 8/2002 | Sirimanne et al. |
| 2002/0188166 A1 | 12/2002 | Viole et al. |
| 2002/0188167 A1 | 12/2002 | Viole et al. |
| 2003/0069468 A1 | 4/2003 | Bolling et al. |

FOREIGN PATENT DOCUMENTS

| | | | | |
|---|---|---|---|---|
| FR | | 2201908 | 10/1972 | ......... A61M/25/00 |
| GB | | 2 174 151 A | 1/1985 | .......... F04B/45/00 |
| JP | | 08257001 A * | 10/1996 | ............ A61B/5/02 |
| WO | | WO 94/05347 | 3/1994 | ............ A61M/1/12 |
| WO | | WO 98/14225 | 3/1997 | ............ A61M/1/10 |
| WO | | WO 97/15228 | 5/1997 | ............ A61B/5/00 |
| WO | | WO 99/19010 | 4/1999 | ............ A61M/1/10 |
| WO | | WO 00/61207 | 10/2000 | ............ A61M/1/10 |
| WO | | WO 02/064204 A1 | 9/2001 | .......... A61M/39/10 |

OTHER PUBLICATIONS

Article: Magnetically Suspended Vad. PP M361, 363, 364.

Article: Mechanical Auxiliary Ventricle. PP M345–344.

Article: A Mechanical Auxiliar Ventricle. PP M340–344.

Patent Server: Patent Search Reports: 15 PP total.

Patent Server: Search Results: 30 PP total.

Article: Effect of Stationary Guiding Vanes on Improvement of the Washout Behind the Rotor in Centrifugal blood Pumps: PP M220–224.

Article: An Implantable Seal—less Centrifugal Pumps: Comparison of Ultrasonic Transit Time and Ultrasonic Doppler Systems: PP 808–815.

Patent Server: Search Reports: 32 PP total.

Article: George J. Magovern. Jr. MD. Use of Biomedics Pump in Postoperative Circulatory Support: 6PP total.

Article: Bruce J. Shook. MS Eng. The Abiomed BVS 5000 Biventricular Support System. 6 PP total.

Article: Valluvan Jeavanandam. MD. Et al. TCI Heartmate Left Ventricular Assist System: Results with Bridge to Transplant and Chronic Support: 5PP total.

Article: O.H. Frazier, MD> Long–Term Ventricular Support with the Heartmate in Patients Undergoing Bridgeto–Transplant Operation: 3PP total.

Article: Narayanan Ramasamy. PhD. Et al.. Novacor LVAS: Results with Bridge to Transplant and Chronic Support: 3PP total.

Article: Robert W. Emery. MD et al. Uses of Mechanical Circulatory Assist Devices at the Minneapolis Heart Institute: 5PP total.

Article: Lawrence R. McBride. MD et al. Anticoagulation in Patients with Ventricular Assist Devices: 1Pg.

Article: Roque Pifarre. MD et al. Bridge to Transplantation with the Total Articical Heart: The Loyal Experience. 5PP total.

Article: Pratap S. Khanwiljkar. MS. MBA et al. Future Prospects for a totally Implantable Artificial Heart: 8 PP total.

Article: Concepts in the Application of Pneumatic Ventricular Assist Devices for Ischemic Myocardial injury. PP 162–168.

Article: Long–Term Left Ventricular Assist Device Use Before Transplantation: PP M530–M534.

Article: In Vitro Characterization of a Magnetically Suspended Continuos Flow Ventricular Assist Device: PP M359–M360.

Article: Estimation of Left Ventricular Function in Patients With a Left Ventricular Assist device: M544–551.

Article: Long Term Follow Up of Survivors of Postcardiotomy Circulatory Support. Ruzevich et al.; 4535, A.S.A.I.O. Transactions 34 (1988) Apr.–Jun., No. 2, Hagerstown, MD, USA, PP 16–124.

Article: Hemodynamic Effects of the Concomitant Use of Intra–Aortic Balloon Pumping and Venoarterial Bypass without Oxygenation in Cardigenic Shock. Takamoto et al. Intra–Aortic Pumping & Ventroaterial Bypass, vol. 19. No. 3, May–Jun. 1972. PP 244–248.

Article: Mechanical Cardiopulmonary Support During Arteriography and Surgical Correction of Coronary Insufficiency Producing Myocardial infarction with Cardiogenic Shok; Carlson et al. Journal of the Association for the Advancement of Medical Instrumentation. vol. 6, No. 3. May–Jun. 1972; PP 244–248.

Article: The Stemotomy Hemopump, A Second Generation Intraarterial Assist Device. PP M218–220, 223.

Article: Transarterial Closed–Chest Left Ventricular (TaCLV) Bypass, PP 386–390.

Article: First Clinical Application of trsnarerial Closed–Chest Left Ventricular (TaCLV)Bypass. PP 386–391.

Article: Implantable Left Ventricular Assist Device. PP 1522–1533.

Article: Effects of Partial and Complete Unloading of The Failing Left Ventricle by Trasnarterial Left ehart Bypass. PP 865–872.

Article: Hydrodynamic Properties of a New Percutaneous Intra–aortic Axial Flow Pump. Reitan et al. ASAIO Journal 2000. pp. 323–328.

Journal of the Association for the Advancement of Medical Instrumentation, vol. 10, No. 5, Sep.–Oct. 1976, p. 215; Medical Instrumentation Editorial.

Dormandy, Goetz, and Kripke; Surgery, Feb. 1969, vol. 65, No. 2, pp. 311–320; Hemodynamics and coronary blood flow with counterpulsation.

The New England Journal of Medicine, Article: Treatment of Severe Fluid Overload by Ultrafiltration, vol. 291, No. 15, Oct. 10, 1974, pp. 747–751.

* cited by examiner

IMPLANTABLE HEART ASSIST SYSTEM AND METHOD OF APPLYING SAME

RELATED APPLICATIONS

This application is a continuation-in-part of U.S. application Ser. No. 10/171,023, filed on Jun. 11, 2002, now U.S. Pat. No. 6,685,621 which is a continuation-in-part of U.S. application Ser. No. 10/078,260, filed on Feb. 15, 2002 now U.S. Pat. No. 6,610,004, which is a continuation-in-part of U.S. application Ser. No. 09/552,979, filed on Apr. 21, 2000, now U.S. Pat. No. 6,390,969 B1, which is a continuation-in-part of U.S. application Ser. No. 09/470,841, filed on Dec. 23, 1999, now U.S. Pat. No. 6,387,037 B1, which is a continuation-in-part of U.S. application Ser. No. 09/289,231, filed on Apr. 9, 1999, now U.S. Pat. No. 6,428,464 B1, which is continuation-in-part of U.S. application Ser. No. 09/166,005, filed on Oct. 2, 1998, now U.S. Pat. No. 6,200,260 B1, which claims the benefit of U.S. Provisional Application Ser. No. 60/061,434, filed Oct. 9, 1997, all of which are hereby expressly incorporated by reference herein in their entirety.

FIELD OF THE INVENTION

The present invention relates generally to a system for assisting the heart and, in particular, to an extracardiac pumping system and a method for both supplementing the circulation of blood through the patient and for enhancing vascular blood mixing using a minimally invasive procedure.

BACKGROUND OF THE INVENTION

During the last decade, congestive heart failure (CHF) has burgeoned into the most important public health problem in cardiovascular medicine. As reported in Gilum, R. F., *Epidemiology of Heart Failure in the U.S.*, 126 Am. Heart J. 1042 (1993), four hundred thousand (400,000) new cases of CHF are diagnosed in the United States annually. The disorder is said to affect nearly 5 million people in this country and close to 20 million people worldwide. The number of hospitalizations for CHF has increased more than three fold in the last 15 years. Unfortunately, nearly 250,000 patients die of heart failure annually. According to the Framingham Heart Study, the 5-year mortality rate for patients with congestive heart failure was 75 per cent in men and 62 per cent in women (Ho, K. K. L., Anderson, K. M., Kannel, W. B., et al., *Survival After the Onset of Congestive Heart Failure in Framingham Heart Study Subject*, 88 Circulation 107 (1993)). This disorder represents the most common discharge diagnosis for patients over 65 years of age. Although the incidence of most cardiovascular disorders has decreased over the past 10 to 20 years, the incidence and prevalence of congestive heart failure has increased at a dramatic rate. This number will increase as patients who would normally die of an acute myocardial infarction (heart attack) survive, and as the population ages.

CHF manifests itself primarily by exertional dyspnea (difficult or labored breathing) and fatigue. Three paradigms are used to describe the causes and therapy of CHF. The first views this condition in terms of altered pump function and abnormal circulatory dynamics. Other models describe it largely in terms of altered myocardial cellular performance or of altered gene expression in the cells of the atrophied heart. In its broadest sense, CHF can be defined as the inability of the heart to pump blood throughout the body at the rate needed to maintain adequate blood flow, and many of the normal functions of the body.

To address CHF, many types of cardiac assist devices have been developed. A cardiac or circulatory assist device is one that aids the failing heart by increasing its pumping function or by allowing it a certain amount of rest to recover its pumping function. Because congestive heart failure may be chronic or acute, different categories of heart assist devices exist. Short of a heart transplant, at least two types of chronic heart assist systems have been developed. One type employs a full or partial prosthetic connected between the heart and the aorta, one example of which is commonly referred to as a LVAD—Left Ventricular Assist Device. With reference to FIG. 1 herein, one example of a LVAD 2 is shown. The LVAD comprises a pump and associated valves 4 that draws blood directly from the apex of the left ventricle 6 and directs the blood to the aortic arch 8, bypassing the aortic valve. In this application, the left ventricle stops functioning and does not contract or expand. The left ventricle becomes, in effect, an extension of the left atrium, with the LVAD 2 taking over for the left ventricle. The ventricle, thus, becomes a low-pressure chamber. Because the intent is to take over for the left ventricle, the LVAD operates by pumping blood at cardiac rates. With an LVAD, oxygenated blood circulation is established sufficient to satisfy the demand of the patient's organs. Under these circumstances, however, continuous flow may not be desired because the patient's arterial system is deprived of pulsatile wave flow, which is beneficial to certain parts of the patient.

Another type of chronic heart assist system is shown in U.S. Pat. No. 5,267,940 to Moulder. Moulder describes a pump implanted into the proximal descending aorta to assist in the circulation of blood through the aorta. Because it is intended to pump blood flowing directly out of the heart, it is important that the Moulder device operate in a properly timed, pulsatile fashion. If it is not operated in direct synchronization with the patient's heart, there is a risk that the pump might cause "carotid steal phenomenon" where blood is drawn away from the patient's brain through the carotid arteries when there is insufficient blood in the left ventricle.

In addressing acute CHF, two types of heart assist devices have been used. One is counterpulsatory in nature and is exemplified by an intra-aortic balloon pump (IABP). With an IABP, the balloon is collapsed during isovolumic contraction, providing a reduced pressure against which the heart must pump blood, thereby reducing the load on the heart during systole. The balloon is then expanded, forcing blood omnidirectionally through the arterial system. Another example of this first type employs one or more collapsible chambers in which blood flows passively into the chamber during systole, as is shown in U.S. Pat. No. 4,240,409 to Robinson et al. The chamber is then collapsed and the blood forcibly returned to the aorta. These devices simulate a chamber of the heart and depend upon an inflatable bladder to effectuate pumping action, requiring an external pneumatic driver. Moreover, they do not operate as a continuous flow system, operating exclusively in pulsatile fashion.

A second type of acute assist device utilizes an extracorporeal pump, such as the Biomedicus centrifugal pump, to direct blood through the patient while surgery is performed on the heart. In one example, described in U.S. Pat. No. 4,968,293 to Nelson, the heart assist system employs a centrifugal pump in which the muscle of the patient is utilized to add pulsatility to the blood flow. The Nelson device is used to bypass a portion of the descending aorta.

Another device, shown in U.S. Pat. No. 4,080,958 to Bregman et al., utilizes an inflatable and collapsible bladder to assist in blood perfusion during heart trauma and is intended to supplement a conventional heart-lung machine by imparting pulsatile actuation. In the primary embodiment disclosed in Bregman, the balloon is controlled to maintain sufficient pressure at the aortic root during diastole to ensure sufficient blood perfusion to the coronary arteries. In an alternative embodiment, a low resistance outlet from the aorta to the inferior vena cava is provided to reduce the aortic pressure during systole, thus, reducing the hemodynamic load on the left ventricle.

Other devices, such as that shown in U.S. Pat. No. 4,034,742 to Thoma, depend upon interaction and coordination with a mechanical pumping chamber containing a movable pumping diaphragm. These devices are intended primarily for application proximate the heart and within the patient's thorax, requiring major invasive surgery.

Many CHF devices are acutely used in the perioperative period. For example, U.S. Pat. No. 4,995,857 to Arnold discloses a perioperative device to pump blood at essentially cardiac rates during surgery when the heart has failed or has been stopped to perform cardiac surgery. The Arnold system temporarily replaces the patient's heart and lung and pumps blood at cardiac rates, typically 5 to 6 liters/min. Like all systems that bypass the heart and the lungs, an oxygenator is required. Of course, with any system that includes an oxygenator, such as the conventional heart-lung machine, the patient cannot be ambulatory.

With early IABP devices, a polyurethane balloon was mounted on a vascular catheter, inserted into the femoral artery, and positioned in the descending aorta just distal to the left subclavian artery. The balloon catheter was connected to a pump console that pumped helium or carbon dioxide into the balloon during diastole to inflate it. During isovolumic contraction, i. e., during the brief time that the aortic valve is closed and the left ventricle continues to contract, the gas used to actuate the balloon was rapidly withdrawn to deflate the balloon. This reduced the pressure at the aortic root when the aortic valve opened. In contrast, during diastole, the balloon was inflated, causing the diastolic pressure to rise and pushing the blood in the aorta distally towards the lower part of the body (on one side of the balloon)and proximally toward the heart and into the coronary arteries (on the other).

The major advantage in such a counterpulsation device was systolic deflation, which lowered the intra-aortic volume and pressure, reducing both afterload and myocardial oxygen consumption. In other words, when the balloon is inflated, it creates an artificially higher pressure in the aorta, which has the ancillary benefit of greater perfusion through the coronary arteries. When the balloon deflates, just before the aortic valve opens, the pressure and volume of the aorta decrease, relieving some of the hemodynamic burden on the heart. These physiologic responses improved the patient's cardiac output and coronary circulation, temporarily improving hemodynamics. In general, counterpulsation with an IABP can augment cardiac output by about 15%, this being frequently sufficient to stabilize the patient's hemodynamic status, which might otherwise rapidly deteriorate. When there is evidence of more efficient pumping ability by the heart, and the patient has moved to an improved class of hemodynamic status, counterpulsation can be discontinued, by slowly weaning while monitoring for deterioration.

Until 1979, all IABP catheters were inserted via surgical cutdown, generally of the femoral artery. Since then, the development of a percutaneous IABP catheter has allowed quicker, and perhaps safer, insertion and has resulted in more expeditious institution of therapy and expansion of clinical applications. Inflation and deflation of the balloon, however, requires a pneumatic pump that is sufficiently large that it must be employed extracorporeally, thereby restricting the patient's movements and ability to carry out normal, daily activities. IABP devices are, thus, limited to short term use, on the order of a few days to a few weeks.

As discussed above, a variety of ventricular assist pumping mechanisms have been designed. Typically associated with LVADs are valves that are used in the inlet and outlet conduits to insure unidirectional blood flow. Given the close proximity of the heart, unidirectional flow was necessary to avoid inadvertent backflow into the heart. The use of such valves also minimized the thrombogenic potential of the LVAD device.

Typically, the pump associated with older LVADs was a bulky pulsatile flow pump, of the pusher plate or diaphragm style, such as those manufactured by Baxter Novacor or TCI, respectively. Given that the pump was implanted within the chest and/or abdominal cavity, major invasive surgery was required. The pumps were typically driven through a percutaneous driveline by a portable external console that monitors and reprograms functions.

Alternatively, rotary pumps, such as centrifugal or axial pumps, have been used in heart assist systems. With centrifugal pumps, the blood enters and exits the pump practically in the same plane. An axial pump, in contrast, directs the blood along the axis of rotation of the rotor. Inspired by the Archimedes screw, one design of an axial pump has been miniaturized to about the size of a pencil eraser, although other designs are larger. Despite its small size, an axial pump may be sufficiently powerful to produce flows that approach those used with older LVADs. Even with miniaturized pumps, however, the pump is typically introduced into the left ventricle through the aortic valve or through the apex of the heart, and its function must be controlled from a console outside the body through percutaneous lines.

All of these heart assist systems referred to above serve one or both of two objectives: (1) to improve the performance of a patient's operative-but-diseased heart from the minimum, classified as NYHAC Class IV, to practically normal, classified as I or 0; or (2) to supplement oxygenated blood circulation through the patient to satisfy organ demand when the patient's heart is suffering from CHF. With such systems, extreme pumping and large amounts of energy, volume, and heat dissipation are required.

Many of these heart assist systems have several general features in common: 1) the devices are cardiac in nature; i. e., they are placed directly within or adjacent to the heart, or within one of the primary vessels associated with the heart (aorta), and are often attached to the heart and/or aorta; 2) the devices attempt to reproduce pulsatile blood flow naturally found in the mammalian circulatory system and, therefore, require valves to prevent backflow; 3) the devices are driven from external consoles, often triggered by the electrocardiogram of the patient; and 4) the size of the blood pump, including its associated connectors and accessories, is generally unmanageable within the anatomy and physiology of the recipient. Due to having one or more of these features, the prior art heart assist devices are limited in their effectiveness and/or practicality.

Many of the above identified prior art systems, generally referred to as Mechanical Circulatory Assist Devices, are not the only means, however, used to treat patients with congestive heart failure (CHF). Most CHF patients are prescribed as many as five to seven different drugs to ameliorate their signs and symptoms. These drugs may include diuretics, angiotensin converting enzyme (ACE) inhibitors, beta-blockers, cardiac glycosides, and peripheral vasodilators. The rationale for pharmacological intervention in heart failure include minimizing the load on the heart, improving the pumping action of the heart by enhancing the contractility of the muscle fibers, and suppression of harmful neurohormonal compensatory mechanisms that are activated because of the decreased pumping function of the heart.

Noncompliance with what is often a complex drug regime may dramatically adversely affect the recovery of a CHF patient leading to the need for hospitalization and possibly morbidity and mortality. In addition, ACE inhibitors and diuretics can cause hypotension, which leads to decreased organ perfusion or an increasing demand on the heart to pump more blood. This leads to an inability, in many cases, to prescribe the most effective dosage of ACE inhibitors and a less than optimum outcome for the patient. Patients suffering from CHF with the underlying cause of mitral valve insufficiency have been able to have their diuretics reduced following surgical repair of their mitral valve. This is due to an increased cardiac output and arterial pressures (as a result of the correction of the problem) resulting in more effective organ perfusion. With the reduction in the use of diuretics and the resultant hypotension, more effective dosages of ACE inhibitors can be used with more favorable outcomes. In addition, it is easier for the patient to follow a less complex drug regime, eliminating the costly and life threatening risks associated with noncompliance.

When blood flow through the coronary arteries falls below the level needed to provide the energy necessary to maintain myocardial function, due often to a blockage in the coronary arteries, a myocardial infarction or heart attack occurs. This is a result of the blockage in the coronary arteries preventing blood from delivering oxygen to tissues downstream of the blockage. The closer the blockage is to the coronary ostia, however, the more severe and life threatening the myocardial infarction. The farther the location of the blockage is from the coronary ostia, the smaller the area of tissue or myocardium that is at risk. As the energy stored in the affected area decreases, myocardial cells begin to die. The larger the area that dies due to the loss of oxygen, the more devastating the infarction. To reduce the area at risk, at least two known options are to either increase the oxygen supply to the affected area or decrease the energy demands of the heart to prolong energy stores until the blockage can be removed or reduced. One particular method to increase blood flow, thereby increasing delivery of oxygen to the affected area, is through a technique called retroperfusion. This is accomplished by passing a cannula into either the right or left ventricle (depending on the area of the blockage) and perfusing oxygenated blood retrograde up the coronary artery on the downstream side of the blockage. Another method is to use drugs to increase the force of contraction of the myocardium, creating increased blood flow across the blocked area. Yet another method is to use drugs, such as pentoxifylline, aspirin, or TPA (tissue plaminogen activator), to reduce the viscosity of (thin out) the blood, inhibit platelet aggregation, or lyse thrombi (clots), respectively, thus, allowing more blood to pass by the blockage. The goal of all of these methods is to increase the delivery of oxygen to the tissue at risk.

The alternative option mentioned above is to reduce the energy demands of the myocardium and increase the amount of time before irreversible damage occurs. This can be accomplished by reducing the workload of the left ventricle (which is the largest energy-consuming portion of the heart). An IABP is placed into the aorta and used as described above, resulting in a decreased afterload on the heart and increased perfusion of the coronary arteries and peripheral organs. An alternative way to reduce myocardial oxygen demand is to reduce the volume of blood the left ventricle must pump. This can be accomplished by reducing the load on the left ventricle, such as in a cardiopulmonary bypass or use of an LVAD. Unloading the left ventricle decreases the energy requirements of the myocardium and increases the amount of time before irreversible damage occurs. This provides an opportunity to more effectively remove or decrease the blockage and salvage myocardial function. To be successful, each of these techniques must be implemented within a short amount of time after the onset of a myocardial infarction. The disadvantage, however, is that each of these techniques can only be performed in an emergency room or hospital setting. Unless the patient is already in the hospital when the myocardial infarction occurs, there is usually some level of irreversible damage and subsequent loss of myocardial function.

There are yet other means of addressing and treating congestive heart failure and related valvular disorders that involve the application of shape change therapies. Those therapies including the use of one or more cardiac reshaping devices designed to squeeze an enlarged heart, or at least an enlarged ventricle within the heart, in an to attempt to restore the heart to its normal healthy size. Such therapy is also designed to maintain the ventricle and/or heart at that normal size while the underlying problem is addressed. By doing so, the therapy results in controlling the physical strain placed on the myocardium caused by a weakened heart and/or a defective heart valve. Such devices are described, for example, in U.S. Pat. No. 6,085,754 to Alferness et al., which discloses a jacket of biological compatible material intended to be placed over the apex of the heart. According to the '754 patent, the heart assumes a maximum adjusted volume for the jacket to constrain circumferential expansion of the heart beyond the maximum adjusted volume during diastole and to permit unimpeded contraction of the heart during systole. Another example is described in U.S. Pat. No. 6,224,540 to Lederman et al., which discloses a passive girdle wrapped around a heart muscle that has dilatation of a ventricle to conform to the size and shape of the heart and to constrain the dilatation during diastole. Other examples are shown in U.S. Pat. No. 6,183,411 to Mortier et al., which discloses alternative configurations including bands, frames and socks and other apparatus formed to fit around an ailing heart to reduce heart wall stress, and in U.S. Pat. Nos. 6,221,103 and 6,190,408, which each disclose a device for restructuring heart chamber geometry. While there may be advantages to using such devices to treat congestive heart failure, there is the disadvantage that it is difficult to determine how far to squeeze the ventricle and/or heart to restore it to its normal size. Moreover, the heart walls are already stressed and enlarged upon the application of such devices. A process of reducing the stress on the heart walls and, thus, the size of the ventricles, prior to applying a restricting device to minimize enlargement during the healing process would be advantageous.

It would be advantageous, therefore, to employ a heart assist system that avoids major invasive surgery and also avoids the use of peripheral equipment that severely restricts a patient's movement. It would also be advantageous to have such a heart assist system that can be employed in a non-hospital setting for ease of treating acute heart problems under emergency conditions. Yet another advantage would be to employ a process of reducing the size of the ventricle and/or the heart, and at the same time the load on the heart, prior to applying a cardiac reshaping device.

SUMMARY OF THE INVENTION

The object of the present invention is to address the aspect of CHF that results from altered pump function and abnormal circulatory dynamics while overcoming the limitations of prior art heart assist systems. Without functioning as a bypass to one or more of a patient's organs, the present invention comprises an extracardiac pumping system for supplementing the circulation of blood through the patient without any component thereof being connected to the patient's heart or primary vessels. Thus, it is extracardiac in nature. With the ability to be applied within a minimally invasive procedure, the present invention significantly improves the condition of the patient suffering from CHF, resulting in the patient feeling much better, even where CHF continues. By supplementing the pumping action of the heart, in lieu of replacing it, the various embodiments of the present invention take advantage of the pulsatile action of the heart, despite its weakened condition, to effectively deliver blood to body organs that benefit from pulsatile delivery of oxygenated blood. As a result, the present invention is capable of being operated in a continuous flow fashion or, if desired, in a pulsatile flow fashion.

An ancillary but important benefit of the present invention is the ability to apply the present invention in such a way as to also reduce the pumping load on the heart and/or to reduce ventricular loading, thereby potentially permitting the heart to recover during use. With the present invention, no bulky pump, valves or oxygenator are required, and no thoracic invasion with major cardiac surgery is required. Indeed, a significant advantage of the present invention is its simplicity while achieving extraordinary results in improving the condition of a patient suffering from CHF. It is contemplated that the present invention be applied such that the heart experiences a reduced pressure at the aortic root during systole (afterload) and/or a reduced left ventricular end diastolic pressure (pre-load), thus reducing the hemodynamic burden or workload on the heart and, thus, permitting the heart to recover. The result is that the present systems and methods described herein have the benefit of reducing ventricular loading.

The extracardiac system of the present invention preferably comprises, in several embodiments, a rotary pump configured to pump blood through the patient at subcardiac rates; i. e., at a flow rate significantly below that of the patient's heart. Other types of pumps or flow generating mechanisms may be effective as well, including but not limited to rotating means, e.g., an Archimedes screw or impeller housed within an open or closed housing, either of which may be cable driven or shaft driven. Pumping the blood tends to revitalize the blood to a certain extent by imparting kinetic and potential energy to the blood discharged from the pump. Importantly, the preferred pump for the present invention pumping system is one that requires a relatively low amount of energy input, when compared to prior art pumps designed to pump at cardiac rates. The pump may be implanted corporeally or more specifically intravascularly, or it may be positioned extracorporeally, depending upon the capability, practicality, or need of the patient to be ambulatory.

The present invention also comprises, in several embodiments, an inflow conduit fluidly coupled to the pump, to direct blood to the pump from a first blood vessel, either the aorta or a first peripheral or non-primary vessel, either directly or indirectly through another blood vessel, wherein insertion of the pump and/or inflow conduit is through a non-primary blood vessel. The invention further comprises an outflow conduit fluidly coupled to the pump, to direct blood from the pump to a second blood vessel, either the aorta or a second peripheral or non-primary blood vessel, whether directly to the second vessel or indirectly through the first or other peripheral or non-primary blood vessel. The connection and/or coupling of the inflow and outflow conduits to the respective blood vessels is performed subcutaneously; not so deep as to involve major invasive surgery. In other words, minimally subdermal. This permits application of the connections in a minimally-invasive procedure. Preferably, the connections to the blood vessels are just below the skin or just below the first layer of muscle, depending upon the blood vessels at issue or the location of the connection, although slightly deeper penetrations may be necessary for some patients or for some applications.

In one embodiment, the present invention is configured so that it may be applied at a single cannulated site and comprises, for example, a multi-lumen catheter having at least one lumen as an inflow lumen and a second lumen as an outlet lumen. The multi-lumen catheter has an inflow port in fluid communication with the inflow lumen. With this embodiment, blood may be drawn into the inflow port of the first lumen from a first peripheral or non-primary blood vessel site, either the blood vessel into which the multi-lumen catheter is inserted or a different blood vessel. The output of the pump directs blood through a second (outlet) port at the distal end of the second lumen that may be located in a second peripheral or non-primary vessel site. This method accomplishes the same beneficial results achieved in the previously described embodiments, but requires only a single cannulated site, rather than two such sites. It should be appreciated that the multi-lumen catheter could be used in a manner where the outflow of the cannula is directed to the first vessel, while the inflow is drawn from the second vessel, Further still, it should be appreciated that in one application the inflow lumen could be positioned to draw blood from a peripheral or non-primary vessel at the site of entry into the patient while the outflow could be positioned in the aorta, proximate an arterial branch.

The pump of the present invention may be a continuous flow pump, a pulsatile pump, and/or a hybrid pump that is configured to generate flow in both a continuous and pulsatile format. The pump may be implantable and is used to fluidly connect two blood vessels, such as the femoral artery at the inflow and the left axillary artery at the outflow, although other peripheral or non-primary arterial and venous blood vessels are contemplated, as well as any singular and/or cumulative combination thereof. An alternative embodiment employs both a continuous flow and a pulsatile flow pump connected in parallel or in series and operating simultaneously or in an alternating fashion. Yet another alternative embodiment employs a rotary pump that is controllable in a synchronous copulsating or counterpulsating fashion, or in some out-of-phase intermediate thereof.

In yet another embodiment, utilizing the benefits of a single site application, the extracardiac system comprises a first conduit comprising more specifically a biocompatible vascular conduit or vascular graft capable of being applied to a blood vessel via an anastomosis connection or some other mechanical connection using biological or synthetic materials. The vascular graft conduit may be entirely synthetic or partially synthetic, with a part intended for intracorporeal use being made with biological material. As with many of the other embodiments described herein, this embodiment may be partially or fully implantable. In the latter instance, the first conduit could be comprised entirely of biological material, as it would be positioned entirely intracorporeally, although it need not be. The first conduit is coupled to a pump designed to pump primarily at subcardiac rates, as described further herein, which is then coupled to a second conduit. Unique to this particular embodiment is an arrangement in which the first conduit is configured to permit the second conduit to pass through the first conduit wall to form an internal lumen between the point of wall penetration and the blood vessel to which the first and second conduit penetrate. The wall penetration may comprise simply a hole in the wall through which the second conduit may pass and to which the second conduit may be sealably secured (to prevent leakage). Alternatively, the wall penetration may comprise a branched conduit with an end that permits the second conduit to pass through and be sealably connected.

It is contemplated that, where the entire system of the present invention is implanted, that it be implanted subcutaneously without the need for major invasive surgery and, preferably, extrathoracically. For example, the pump may be implanted in the groin area, with the inflow conduit attached to the femoral or iliac artery proximate thereto and the outflow conduit attached to the axillary artery proximate the shoulder. It is contemplated that the outflow conduit be applied by tunneling it under the skin from the pump to the axillary artery. Alternatively, the pump and conduits may be applied intravascularly through a non-primary blood vessel in a subcutaneous application. In such an embodiment, the pump is sized and configured to be positioned within or pass through a non-primary vessel and introduced via a percutaneous insertion or a surgical cutdown with or without accompanying inflow and outflow conduits. The pump may be enclosed within a conduit through which blood may be directed, an open housing having a cage-like arrangement to shield the pump blades from damaging the endothelial lining, or a closed housing having an inlet and outlet to which inflow and outflow conduits may be respectively attached.

Where implanted, the pump is preferably powered by an implantable power source, such as for example a battery, that may be regenerated externally by an RF induction system or be replaced periodically, and/or a self-generating power source that, for example, draws energy from the human body (e. g., muscles, chemicals, heat). The pump may alternatively be powered by a rotatably driven cable extending and controlled extracorporeally.

The present invention also comprises a method for supplementing the circulation of blood in the patient and potentially reducing the workload on the heart of a patient without connecting any component to the patient's heart. The inventive method comprises the steps of using a pump configured to generate blood flow at volumetric rates that are on average subcardiac, wherein the pump, whether implantable or not, may have an inflow and outflow conduit attached thereto and may be enclosed in an open or closed housing; fluidly coupling a distal end of the inflow conduit to a first peripheral or non-primary blood vessel with a minimally-invasive surgical procedure to permit the flow of blood to the pump from the first peripheral or non-primary blood vessel of the patient; implanting the inflow conduit subcutaneously; fluidly coupling a distal end of the outflow conduit to a second or same blood vessel, whether primary or non-primary, with a minimally-invasive surgical procedure to permit the flow of blood away from the pump to the second blood vessel of the patient; and operating said pump to perfuse blood through the patient's circulatory system. Equally valuable, the method could also involve withdrawing blood from a primary blood vessel and discharging the blood into a non-primary blood vessel. "Fluid coupling" to a primary vessel referred to herein refers to positioning the distal end of an inflow or outflow conduit within a desired primary vessel for withdraw or discharge of blood therein. Fluid coupling to a non-primary vessel referred to herein refers to one of either positioning the distal end of a conduit within the desired blood vessel, applying a catheter percutaneously or through surgical cut-down, or connecting the conduit to the vessel via an anastomosis procedure or other connection, where the conduit functions as a graft. Where the desired peripheral or non-primary blood vessel is the axillary artery, the step of connecting the distal end of the outflow conduit may be performed in such a manner that a sufficient flow of blood is directed toward the hand to avoid limb ischemia while ensuring that sufficient flow is directed toward the aorta without damaging the endothelial lining of the axillary vessel. The same concerns for avoiding limb ischemia and damage to the endothelial lining would apply, however, regardless of the selection of second peripheral or non-primary blood vessel.

In one specific application, the pump is capable of synchronous control wherein the step of operating the pump includes the steps of beginning discharge of blood out of the pump during isovolumic contraction and discontinuing discharge of blood when the aortic valve closes following systole. Depending upon the patient and the specific arrangement of the present system, this specific method results in reduced afterload and/or preload on the heart while also supplementing circulation. For example, in one application, the first and second blood vessels are the femoral and axillary arteries, respectively; or the femoral artery and the aorta, respectively. Numerous other combinations may be equally effective to achieve the benefits of the present invention.

In an alternative method of applying the present invention, the pump is not implanted and the inflow and outflow conduits are fluidly coupled to the first and second blood vessels percutaneously, using a readily-removable connector, such as a cannula, to connect the distal ends of each conduit to the blood vessels.

The present invention further comprises a method that comprises the steps of applying a proximal end of a vascular graft first conduit to a pump and a distal end of the first conduit to a non-primary blood vessel via an anastomosis connection or other connection; fluidly coupling a second conduit, which is connected at a proximal end to the pump, through the vascular graft first conduit to a non-primary blood vessel so as to form a multi-lumen arrangement; and operating the pump to draw blood from one non-primary blood vessel and returning it to the same or different blood vessel at subcardiac rates to supplement blood perfusion. The step of fluidly coupling the second conduit to a non-primary blood vessel may comprise attaching the second conduit to the first conduit and to the pump, where the first conduit is preconfigured to comprise a multi-lumen catheter between the point of connection and the distal end of the first conduit, or it may comprise inserting a cannula end of the second conduit through an opening in the wall of the first conduit and passing it through the first conduit and into the blood vessel to reside in that same blood vessel or a different blood vessel.

In yet a different application of the present inventive methods, the method includes the steps of, prior to applying a shape change therapy involving a cardiac reshaping device, applying a blood supplementation system to the patient that is designed to reduce the size or wall stress of one or both of the ventricles that results in a reduction in ventricular loading, including the steps of providing a pump configured to pump blood at subcardiac rates, providing inflow and outflow conduits configured to fluidly communicate with one or more non-primary blood vessels, connecting the inflow conduit to a non-primary blood vessel, connecting the outflow conduit to the same or different blood vessel and operating the subcardiac pump in a manner, as described herein, to reduce the size and/or wall stress (ventricular load). The method further comprises, after sufficient reduction in ventricular load, applying a cardiac reshaping device, such as those referred to herein, or another capable of serving the same or substantially similar function.

An important advantage of the present invention is that it utilizes the benefits of an IABP, without the requirement of extracorporeal equipment or the need to have a balloon or similar implement partially obstructing a blood vessel. In addition to the benefits of an IABP, it also offers the benefit of reducing the preload on the heart. The present invention thus offers simplicity and long-term use.

Another important advantage of the present invention is its potential to enhance mixing of systemic arterial blood, particularly in the aorta, and thereby deliver blood with a higher oxygen-carrying capacity to organs supplied by arterial side branches off of the aorta. This overcomes the problem of blood streaming in the descending aorta that may sometimes occur in patients suffering from low cardiac output or other ailments resulting in low blood flow. The lack of mixing of the blood within the descending aorta that may result from blood streaming could lead to a higher concentration of red blood cells and nutrients in the central region of the aorta and a decreasing concentration of red blood cells closer to the aortic wall. This could result in lower hematocrit blood flowing into branch arteries from the aorta. Where it is desired to address the potential problem of blood streaming, a method of utilizing the present invention may include taking steps to assess certain parameters of the patient and then to determine the minimum output of the pump that ensures turbulent flow in the aorta, thereby enhancing blood mixing. One embodiment of that method includes the step of determining the Reynolds number and the average Womersley number for the flow through the descending aorta before and/or after applying the present inventive system to the patient and adjusting the pump accordingly.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENTS

Turning now to the drawings provided herein, a more detailed description of the embodiments of the present invention is provided below. It should be noted, however, that while some embodiments have all of the advantages identified herein, other embodiments may only realize some but not all of the advantages.

The present invention provides a heart assist system that is extracardiac in nature. In other words, the present invention supplements blood perfusion, without the need to interface directly with the heart and aorta. Thus, no major invasive surgery is necessary to use the present invention. The present invention also lessens the hemodynamic burden or workload on the heart by reducing the pressure at the aortic root during systole (afterload) and/or reducing left ventricular end diastolic pressure and volume (preload).

Figure 1:
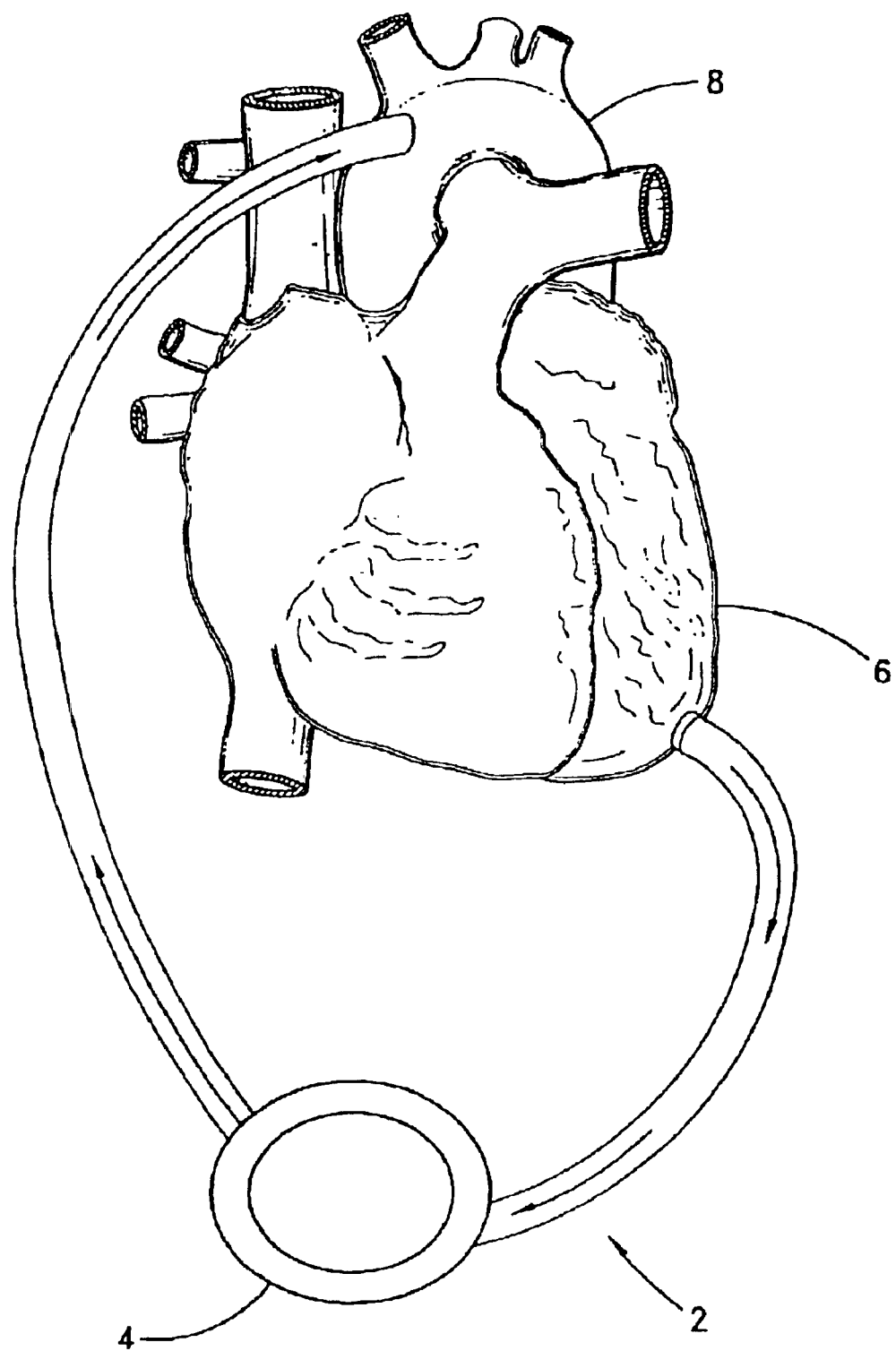
FIG. 1 is a schematic view of a cardiac assist device, known as a left ventricular assist device, showing a bypass from the apex of the left ventricle to the aortic arch.
Figure 2:
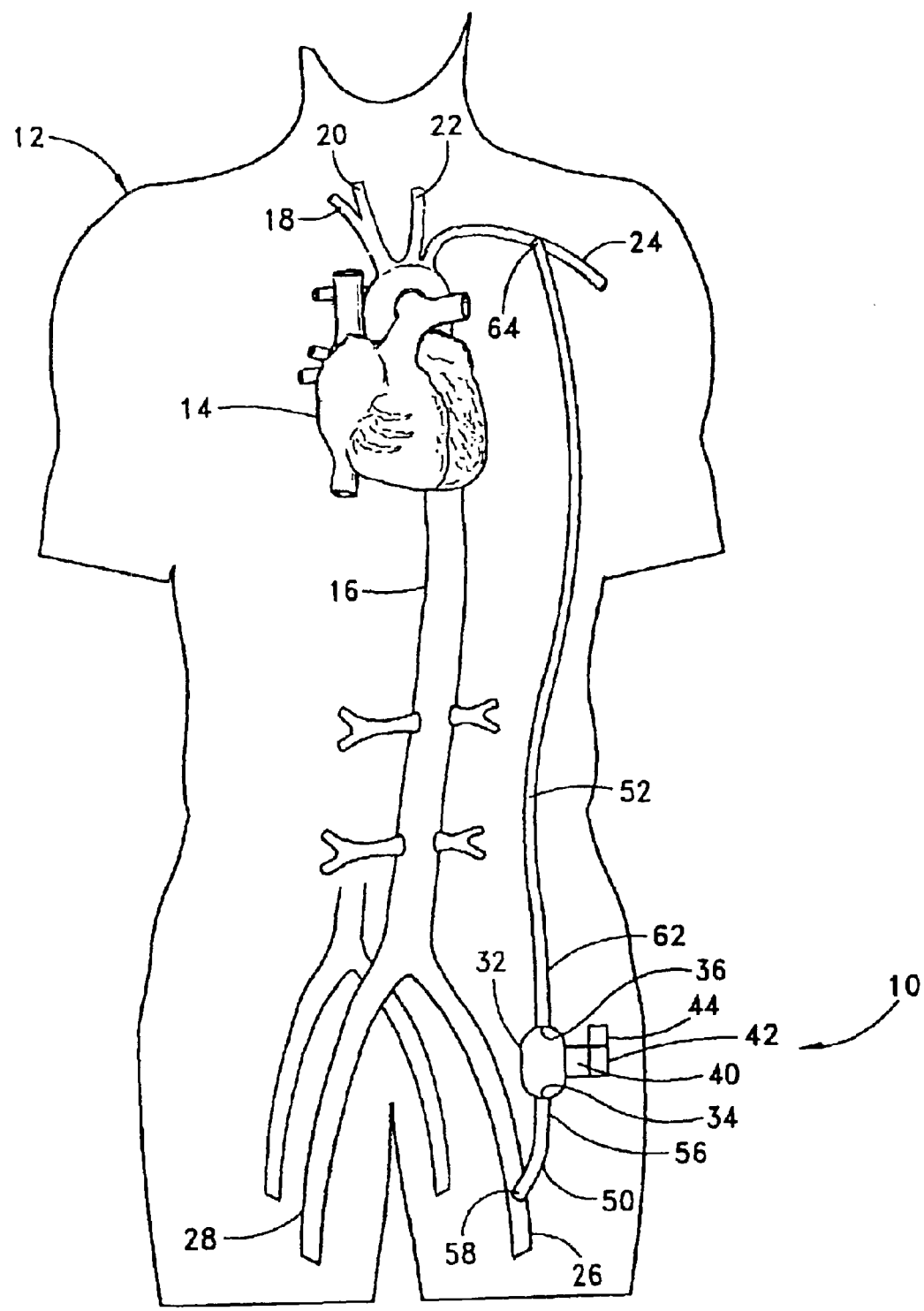
FIG. 2 is a schematic view of a first embodiment of the present invention, shown applied to a patient's circulatory system.

With reference to FIG. 2, a first embodiment of the present invention 10 is shown applied to a patient 12 having an ailing heart 14 and an aorta 16, from which peripheral brachiocephalic blood vessels extend, including the right subclavian 18, the right carotid 20, the left carotid 22, and the left axillary 24. Extending from the descending aorta is another set of peripheral blood vessels, the left and right femoral arteries 26, 28.

The first embodiment 10 comprises a pump 32, having an inlet 34 and an outlet 36 for connection of flexible conduits thereto. The pump 32 is preferably a rotary pump, either an axial type or a centrifugal type, although other types of pumps may be used, whether commercially-available or customized. In either case, the pump should be sufficiently small to be implanted subcutaneously and preferably extrathoracically, for example in the groin area of the patient, without the need for major invasive surgery. Because the present invention is an extracardiac system, no valves are necessary. Any inadvertent backflow through the pump and/or through the inflow conduit would not harm the patient.

Regardless of the style or nature chosen, the pump 32 of the present invention is sized to generate blood flow at subcardiac volumetric rates, less than about 50% of the flow rate of an average healthy heart, although flow rates above that may be effective. Thus, the pump 32 of the present invention is sized and configured to discharge blood at volumetric flow rates anywhere in the range of 0.1 to 3 liters per minute, depending upon the application desired and/or the degree of need for heart assist. For example, for a patient experiencing advanced congestive heart failure, it may be preferable to employ a pump that has an average subcardiac rate of 2.5 to 3 liters per minute. In other patients, particularly those with minimal levels of heart failure, it may be preferable to employ a pump that has an average subcardiac rate of 0.5 liters per minute or less. In yet other patients it may be preferable to employ a pump that is a pressure wave generator that uses pressure to augment the flow of blood generated by the heart.

In one embodiment, the pump selected is a continuous flow pump so that blood perfusion through the circulation system is continuous. In an alternative embodiment, the pump selected has the capability of synchronous actuation; i. e., it may be actuated in a pulsatile mode, either in copulsating or counterpulsating fashion.

For copulsating action, it is contemplated that the pump 32 would be actuated to discharge blood generally during systole, beginning actuation, for example, during isovolumic contraction before the aortic valve opens or as the aortic valve opens. The pump would be static while the aortic valve is closed following systole, ceasing actuation, for example, when the aortic valve closes.

For counterpulsating actuation, it is contemplated that the pump 32 would be actuated generally during diastole, ceasing actuation, for example, before or during isovolumic contraction. Such an application would permit and/or enhance coronary blood perfusion. In this application, it is contemplated that the pump would be static during the balance of systole after the aortic valve is opened, to lessen the burden against which the heart must pump. The aortic valve being open encompasses the periods of opening and closing, wherein blood is flowing therethrough.

It should be recognized that the designations copulsating and counterpulsating are general identifiers and are not limited to specific points in the patient's heart cycle when the pump begins and discontinues actuation. Rather, they are intended to generally refer to pump actuation in which the pump is actuating, at least in part, during systole and diastole, respectively. For example, it is contemplated that the pump might be activated to be out of phase from true copulsating or counterpulsating actuation described herein, and still be synchronous, depending upon the specific needs of the patient or the desired outcome. One might shift actuation of the pump to begin prior to or after isovolumic contraction or to begin before or after isovolumic expansion.

Furthermore, the pulsatile pump may be actuated to pulsate asynchronously with the patient's heart. Typically, where the patient's heart is beating irregularly, there may be a desire to pulsate the pump asynchronously so that the perfusion of blood by the extracardiac pumping system is more regular and, thus, more effective at oxygenating the organs. Where the patient's heart beats regularly, but weakly, synchronous pulsation of the extracardiac pump may be preferred.

The pump 32 is driven by a motor 40 and/or other type of drive means and is controlled preferably by a programmable controller 42 that is capable of actuating the pump in pulsatile fashion, where desired, and also of controlling the speed or output of the pump. For synchronous control, the patient's heart would preferably be monitored with an EKG in which feedback would be provided the controller 42. The controller 42 is preferably programmed by the use of external means. This may be accomplished, for example, using RF telemetry circuits of the type commonly used within implantable pacemakers and defibrillators. The controller may also be autoregulating to permit automatic regulation of the speed, and/or regulation of the synchronous or asynchronous pulsation of the pump, based upon feedback from ambient sensors monitoring parameters, such as pressure or the patient's EKG. It is also contemplated that a reverse-direction pump be utilized, if desired, in which the controller is capable of reversing the direction of either the drive means or the impellers of the pump. Such a pump might be used where it is desirable to have the option of reversing the direction of circulation between two peripheral blood vessels.

Power to the motor 40 and controller 42 may be provided by a power source 44, such as a battery, that is preferably rechargeable by an external induction source (not shown), such as an RF induction coil that may be electromagnetically coupled to the battery to induce a charge therein. Alternative power sources are also possible, including a device that draws energy directly from the patient's body; e. g., the patient's muscles, chemicals or heat. The pump can be temporarily stopped during recharging with no appreciable life threatening effect, because the system only supplements the heart, rather than substituting for the heart.

While the controller 42 and power source 44 are preferably pre-assembled to the pump 32 and implanted therewith, it is also contemplated that the pump 32 and motor 40 be implanted at one location and the controller 42 and power source 44 be implanted in a separate location. In one alternative arrangement, the pump 32 may be driven externally through a percutaneous drive line. In another alternative, the pump, motor and controller may be implanted and powered by an extracorporeal power source. In the latter case, the power source could be attached to the side of the patient to permit fully ambulatory movement.

The inlet 34 of the pump 32 is preferably connected to a flexible inflow conduit 50 and a flexible outflow conduit 52 to direct blood flow from one peripheral blood vessel to another. The inflow and outflow conduits 50, 52 may, for example, be formed from Dacron, Hemashield or Gortex materials, although other synthetic materials may be suitable. The inflow and outflow conduits 50, 52 may also comprise biologic materials or pseudobiological (hybrid) materials (e. g., biologic tissue supported on a synthetic scaffold). The inflow and outflow conduits are preferably configured to minimize kinks so blood flow is not meaningfully interrupted by normal movements of the patient or compressed easily from external forces. In some cases, the inflow and/or outflow conduits may come commercially already attached to the pump. Where it is desired to implant the pump 32 and the conduits 50, 52, it is preferable that the inner diameter of the conduits be less than 25 mm, although diameters slightly larger may be effective.

Figure 11:
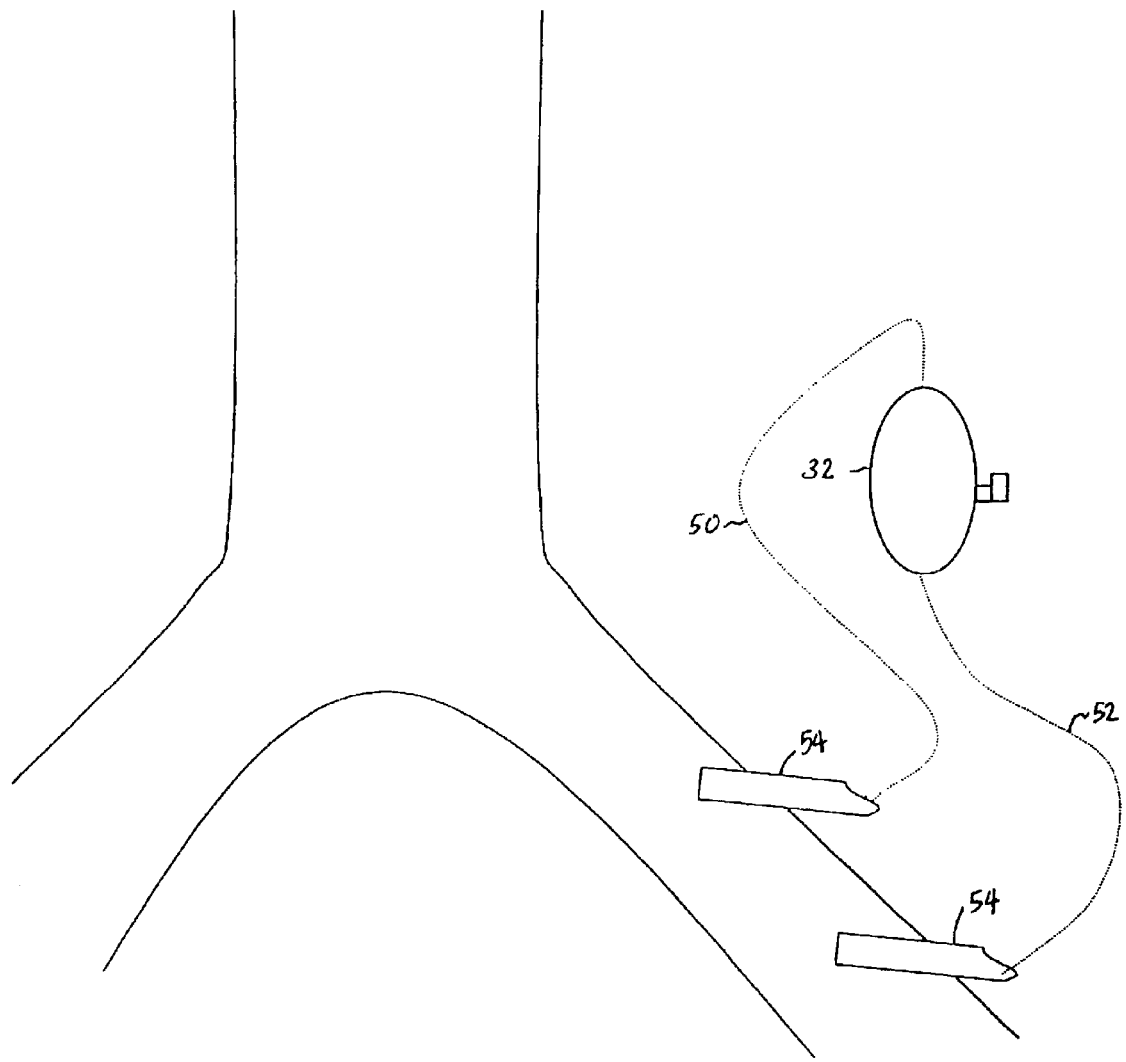
FIG. 11 is a schematic view of an application of the embodiment of FIG. 2 in which the inflow conduit and outflow conduit are applied to the same non-primary blood vessel.

In one preferred application of the present invention, the first embodiment is applied in an arterial-arterial fashion; for example, as a femoral-axillary connection, as is shown in FIG. 2. It should be appreciated by one of ordinary skill in the art that an axillary-femoral connection would also be effective using the embodiments described herein. Indeed, it should be recognized by one of ordinary skill in the art that the present invention might be applied to any of the peripheral blood vessels in the patient. In an alternative arrangement, as shown in FIG. 11, the first embodiment may be applied so that the inflow conduit and the outflow conduit are applied subcutaneously to the same non-primary vessel, in any manner described herein.

The inflow conduit 50 has a first proximal end 56 that connects with the inlet 34 of the pump 32 and a second distal end 58 that connects with a first peripheral blood vessel, which is preferably the left femoral artery 26 of the patient 12, although the right femoral artery or any other peripheral artery may be acceptable. In one application, the connection between the inflow conduit 50 and the first blood vessel is via an end-to-side anastomosis, although a side-to-side anastomosis connection might be used mid-stream of the conduit where the inflow conduit were connected at its second end to an additional blood vessel or at another location on the same blood vessel (neither shown).

Similarly, the outflow conduit 52 has a first proximal end 62 that connects to the outlet 36 of the pump 32 and a second distal end 64 that connects with a second peripheral blood vessel, preferably the left axillary artery 24 of the patient 12, although the right axillary artery, or any other peripheral artery, would be acceptable. In one application, the connection between the outflow conduit 52 and the second blood vessel is via an end-to-side anastomosis, although a side-to-side anastomosis connection might be used mid-stream of the conduit where the outflow conduit were connected at its second end to yet another blood vessel (not shown) or at another location on the same blood vessel. Preferably, the outflow conduit is attached to the second blood vessel at an angle that results in the predominant flow of blood out of the pump proximally toward the aorta and heart, such as is shown in FIG. 2, while still maintaining sufficient flow distally toward the hand to prevent limb ischemia.

It is preferred that application of the present invention to the peripheral or non-primary blood vessels be accomplished subcutaneously; i.e., at a shallow depth just below the skin or first muscle layer so as to avoid major invasive surgery. It is also preferred that the present invention be applied extrathoracically to avoid the need to invade the patient's chest cavity. Where desired, the entire extracardiac system of the present invention 10 may be implanted within the patient 12, either extravascularly or intravascularly or a hybrid thereof. In the case of an extravascular application, the pump 32 may be implanted, for example, into the groin area, with the inflow conduit 50 fluidly connected subcutaneously to, for example, the femoral artery 26 proximate the pump 32. The outflow conduit would be tunneled subcutaneously through to, for example, the left axillary artery 24. In an alternative arrangement, the pump 32 and associated drive and controller could be temporarily fastened to the exterior skin of the patient, with the inflow and outflow conduits 50, 52 connected percutaneously. In either case, the patient may be ambulatory without restriction of tethered lines.

Referring to FIG. 11, an alternative method of using the present invention comprises the steps of fluidly coupling the inflow conduit 50, which is fluidly coupled to pump 32, to a patient subcutaneously to a non-primary blood vessel, either via an anastomosis connection or percutaneously with a cannula 54, fluidly coupling the outflow conduit 52 to the same blood vessel in a desired manner described herein, directing blood from the blood vessel through the inflow conduit, through the pump and the outflow conduit into the blood vessel. In the application of FIG. 11, the system is positioned at the patient's left femoral artery. Specific applications of this alternative method may further comprise positioning the inflow conduit upstream of the outflow conduit, although the reverse arrangement is also contemplated. It is also contemplated that either the inflow conduit or the outflow conduit may extend through the non-primary blood vessel to a second blood vessel (e.g., through the left femoral to the aorta proximate the renal branch) so that blood may be directed from the first to the second blood vessel or vice versa.

Figure 3:
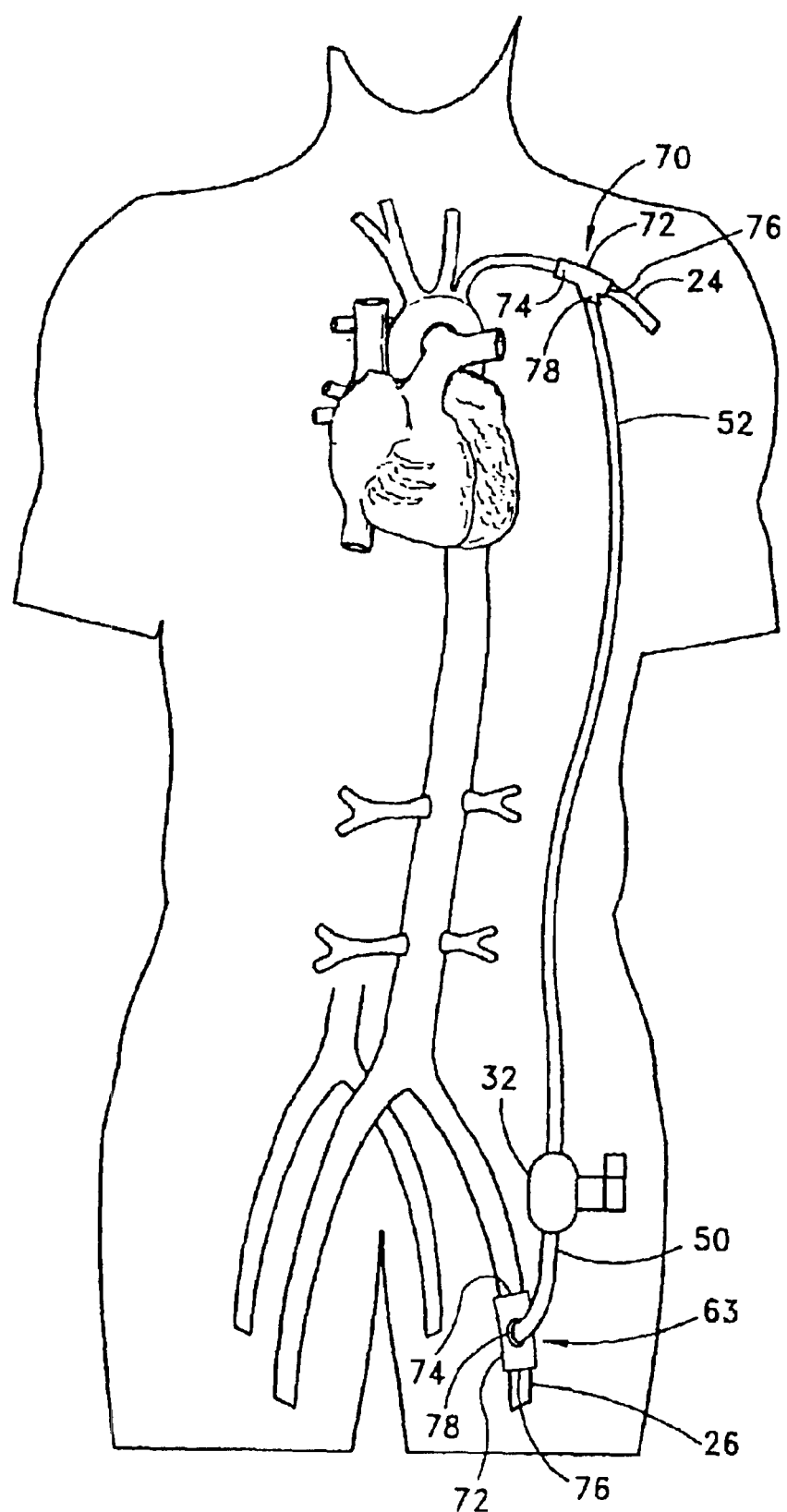
FIG. 3 is a schematic view of a second embodiment of the present invention, shown applied to a patient's circulatory system.

It is contemplated that, where an anastomosis connection is not desired, a special connector may be used to connect the conduits 50, 52 to the peripheral blood vessels. With reference to FIG. 3, a second embodiment of the present invention is shown, wherein the inflow conduit 50 and outflow conduit 52 are connected to the peripheral blood vessels via first and second connectors 68, 70 each comprising three-opening fittings. In the preferred embodiment, the connectors 68, 70 comprise an intra-vascular, generally-tee-shaped fitting 72 having a proximal end 74, a distal end 76, and an angled divergence 78 permitting connection to the inflow and outflow conduits 50, 52 and the blood vessels. The proximal and distal ends 74, 76 of the fittings 72 permit connection to the blood vessel into which the fitting is positioned. The angle of divergence 78 of the fittings 72 may be 90 degrees or less in either direction from the axis of flow through the blood vessel, as optimally selected to generate the needed flow distally toward the hand to prevent limb ischemia, and to insure sufficient flow and pressure toward the aorta to provide the circulatory assistance and workload reduction needed while minimizing or avoiding endothelial damage to the vessel. In another embodiment, the connectors 68, 70 are sleeves (not shown) that surround and attach to the outside of the peripheral blood vessel where, within the interior of the sleeve, a port to the blood vessel is provided to permit blood flow from the conduits 50, 52 when they are connected to the connectors 68, 70, respectively.

Figure 7:
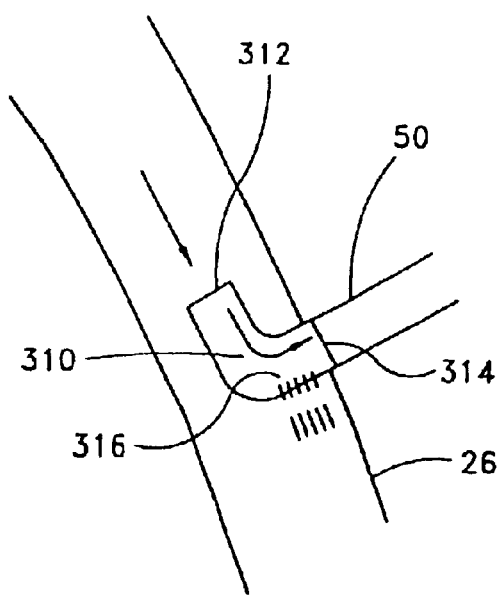
FIG. 7 is a schematic view of an inflow L-shaped connector, shown inserted within a blood vessel.

Other types of connectors having other configurations are contemplated that may avoid the need for an anastomosis connection or that permit connection of the conduits to the blood vessels. For example, it is contemplated that an L-shaped connector be used if it is desired to withdraw blood more predominantly from one direction of a peripheral vessel or to direct blood more predominantly into a peripheral vessel. Referring to FIG. 7, an inflow conduit 50 is fluidly connected to a peripheral vessel, for example, the left femoral artery 26, using an L-shaped connector 310. The connector 310 has an inlet port 312 at a proximal end and an outlet port 314 through which blood flows into the inflow conduit 50. The connector 310 also has an arrangement of holes 316 within a wall positioned at a distal end opposite the inlet port 312 so that some of the flow drawn into the connector 310 is diverted through the holes 312, particularly downstream of the connector, as in this application. A single hole in the wall could also be effective, depending upon size and placement. The connector may be a deformable L-shaped catheter percutaneously applied to the blood vessel or, in an alternative embodiment, be connected directly to the walls of the blood vessel for more long term application. By directing some blood flow downstream of the connector during withdrawal of blood from the vessel, ischemic damage downstream from the connector may be avoided. Such ischemic damage might otherwise occur if the majority of the blood flowing into the inflow connector were diverted from the blood vessel into the inflow conduit. It is also contemplated that a connection to the blood vessels might be made via a cannula, wherein the cannula is implanted, along with the inflow and outflow conduits.

The advantage of discrete connectors is their potential application to patients with chronic CHF. A connector eliminates a need for an anastomosis connection between the conduits of the present invention system and the peripheral blood vessels where it is desired to remove and/or replace the system more than one time. The connectors could be applied to the first and second blood vessels semi-permanently, with an end cap applied to the divergence for later quick-connection of the present invention system to the patient. In this regard, a patient might experience the benefit of the present invention periodically, without having to reconnect and redisconnect the conduits from the blood vessels via an anastomosis procedure each time. Each time it is desired to implement the present invention, the end caps would be removed and the conduit attached to the connectors quickly.

In the preferred embodiment of the connector 70, the divergence 78 is oriented at an acute angle significantly less than 90° from the axis of the fitting 72, as shown in FIG. 3, so that a majority of the blood flowing through the outflow conduit 52 into the blood vessel (e. g., left axillary 24) flows in a direction proximally toward the heart 14, rather than in the distal direction. In an alternative embodiment, the proximal end 74 of the fitting 72 may have a diameter larger than the diameter of the distal end 76, without need of having an angled divergence, to achieve the same result.

With or without a connector, with blood flow directed proximally toward the aorta, the result may be concurrent flow down the descending aorta, which will result in the reduction of pressure at the aortic root. Thus, the present invention may be applied so to reduce the afterload on the patient's heart, permitting at least partial if not complete CHF recovery, while supplementing blood circulation. Concurrent flow depends upon the phase of operation of the pulsatile pump and the choice of second blood vessel to which the outflow conduit is connected.

Figure 4:
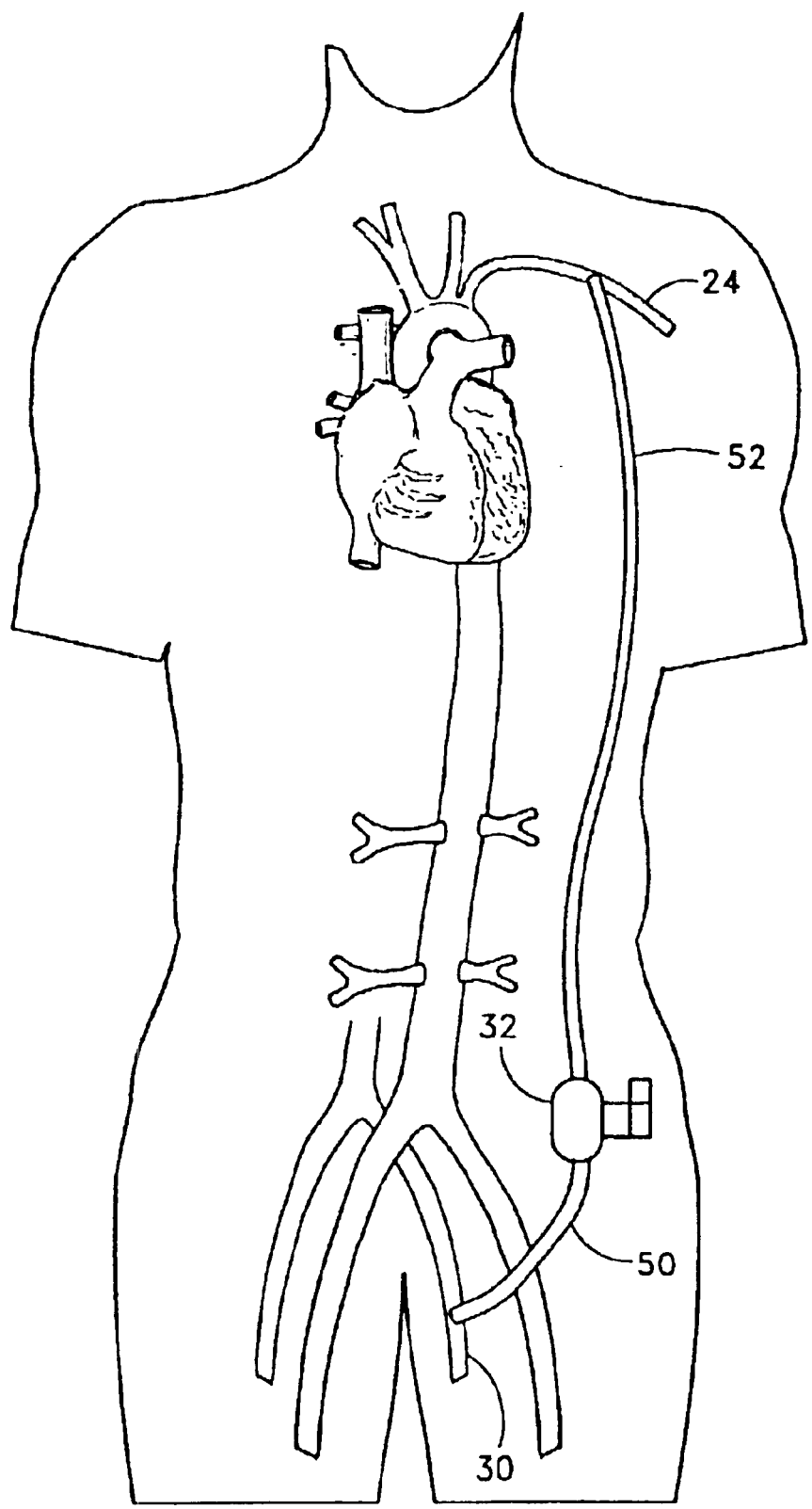
FIG. 4 is a schematic view of a variation of the first embodiment of FIG. 2 shown implanted into a patient.

While the present invention may be applied to create an arterial-arterial flow path, given the nature of the present invention, i. e., supplementation of circulation to meet organ demand, a venous-arterial flow path may also be used. For example, with reference to FIG. 4, one embodiment of the present invention 10 may be applied to the patient 12 such that the inflow conduit 50 is connected to a peripheral vein, such as the left femoral vein 80. In this arrangement, the outflow conduit 50 may be connected to one of the peripheral arteries, such as the left axillary 24. Arterial-venous arrangements are contemplated as well. In those venous-arterial cases where the inflow is connected to a vein and the outflow is connected to an artery, the pump 32 should be sized to permit flow sufficiently small so that oxygen-deficient blood does not rise to unacceptable levels in the arteries. It should be appreciated that the connections to the peripheral veins could be by one or more methods described above for connecting to a peripheral artery. It should also be appreciated that the present invention could be applied as a venous-venous flow path, wherein the inflow and outflow are connected to separate peripheral veins. In addition, an alternative embodiment comprises two discrete pumps and conduit arrangements, one being applied as a venous-venous flow path, and the other as an arterial-arterial flow path.

When venous blood is mixed with arterial blood either at the inlet of the pump or the outlet of the pump the ratio of venous blood to arterial blood should be controlled to maintain an arterial saturation of a minimum of 80% at the pump inlet or outlet. Arterial saturation can be measured and/or monitored by pulse oximetry, laser doppler, colorimetry or other methods used to monitor blood oxygen saturation. The venous blood flow into the system can then be controlled by regulating the amount of blood allowed to pass through the conduit from the venous-side connection.

Figure 5:
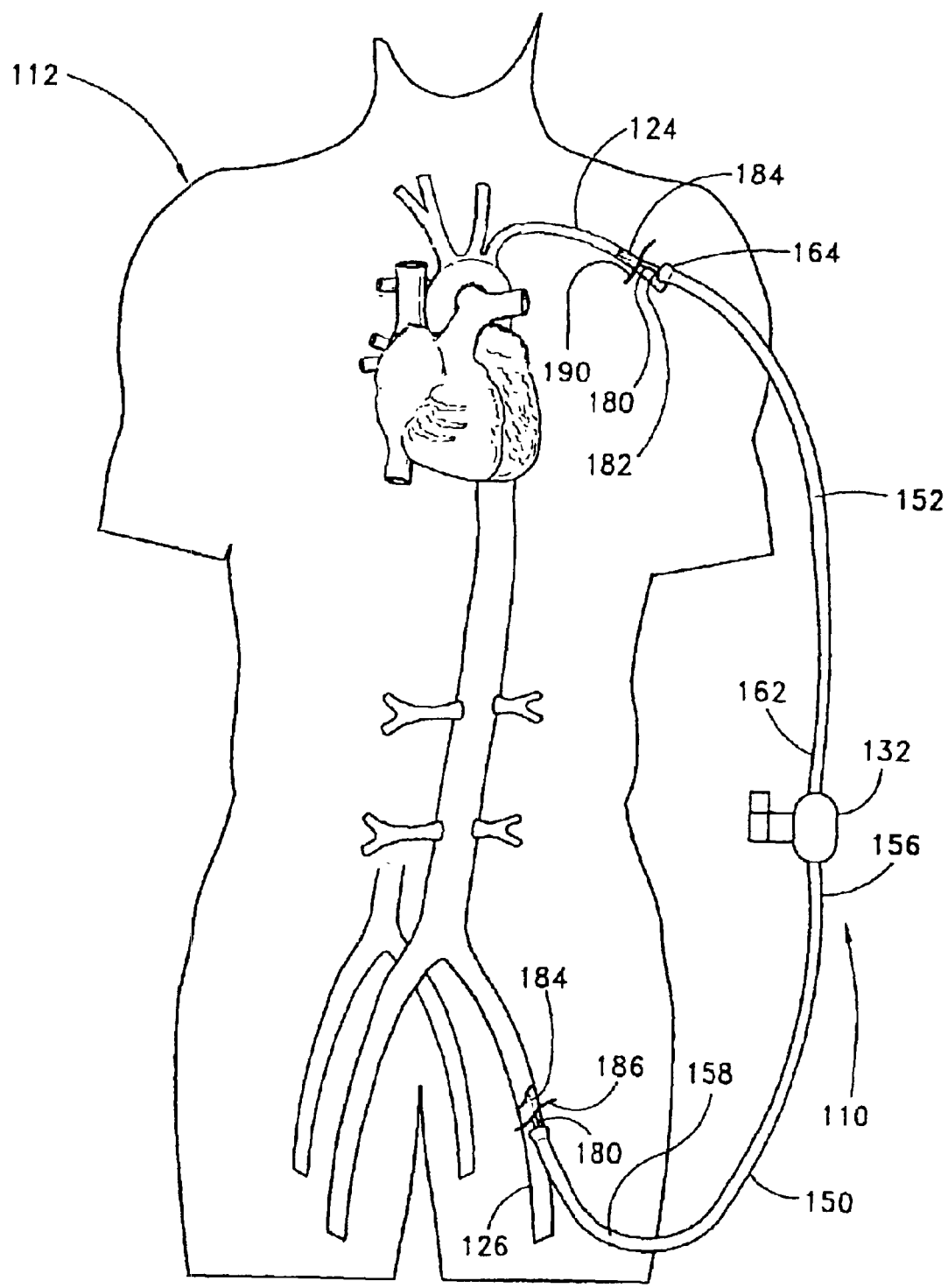
FIG. 5 is a schematic view of a third embodiment of the present invention, shown applied to a patient's circulatory system.
Figure 10:
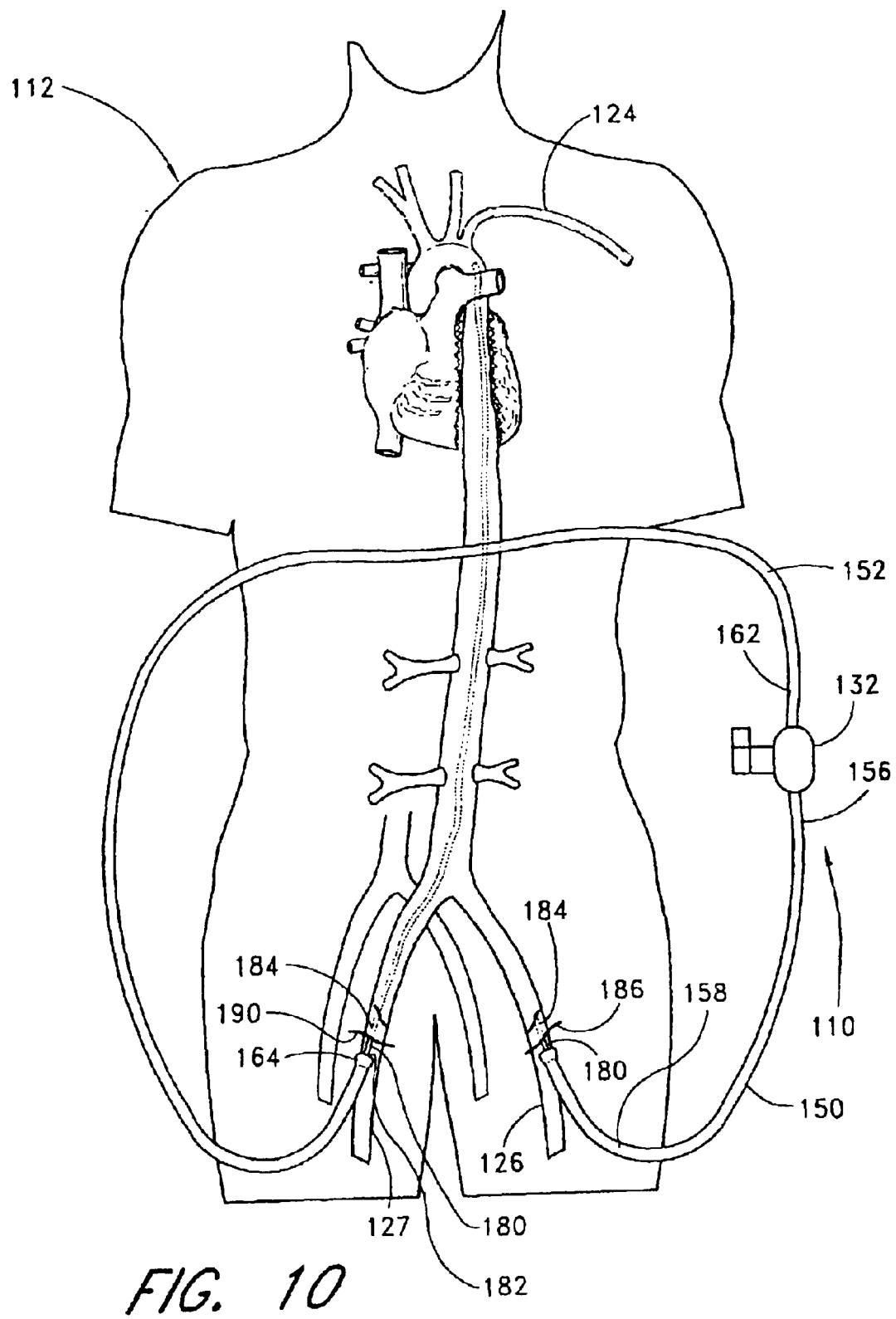
FIG. 10 is a schematic view of a variation of the third embodiment of FIG. 5, shown applied to a patient's circulatory system.

A partial external application of the present invention is contemplated where a patient's heart failure is acute; i. e., is not expected to last long, or in the earlier stages of heart failure (where the patient is in New York Heart Association Classification (NYHAC) functional classes II or III). With reference to FIGS. 5 and 10, a third embodiment of the present invention 110 is applied percutaneously to a patient 112 to connect two peripheral blood vessels wherein a pump 132 and its associated driving means and controls are employed extracorporeally. The pump 132 has an inflow conduit 150 and an outflow conduit 152 associated therewith for connection to two peripheral blood vessels. The inflow conduit 150 has a first end 156 and second end 158 wherein the second end is connected to a first peripheral blood vessel (e. g., femoral artery 126) by way of a cannula 180. The cannula 180 has a first end 182 sealably connected to the second end 158 of the inflow conduit 150. The cannula 180 also has a second end 184 that is inserted through a surgical opening 186 or an introducer sheath (not shown) and into the blood vessel source (e.g., femoral artery 126).

Similarly, the outflow conduit 152 has a first end 162 and second end 164 wherein the second end is connected to a second peripheral blood vessel (e. g., left axillary artery 124, as shown in FIG. 5, or the right femoral 127, as shown in FIG. 10) by way of a cannula 180. Like the inflow cannula, the outflow cannula 180 has a first end 182 sealably connected to the second end 164 of the outflow conduit 152. The outflow cannula 180 also has a second end 184 that is inserted through surgical opening 190 or an introducer sheath (not shown) and into the second blood vessel (e. g., left axillary artery 124 or right femoral 127). As shown in FIG. 10, the second end 184 of the outflow cannula may extend well into the aorta, for example, proximal to the left subclavian. If desired, it may also terminate within the left subclavian artery or the left axillary artery, or it may terminate in the mesenteric or renal arteries (not shown), where in either case, the cannula has passed through at least a portion of a primary artery (in this case, the aorta). Also, if desired, blood drawn into the extracardiac system described herein may originate from the descending aorta (or an artery branching therefrom) and be directed into a blood vessel that is neither the aorta nor pulmonary artery. By use of a percutaneous application, the present invention may be applied temporarily without the need to implant any aspect thereof or to make anastomosis connections to the blood vessels.

Figure 9:
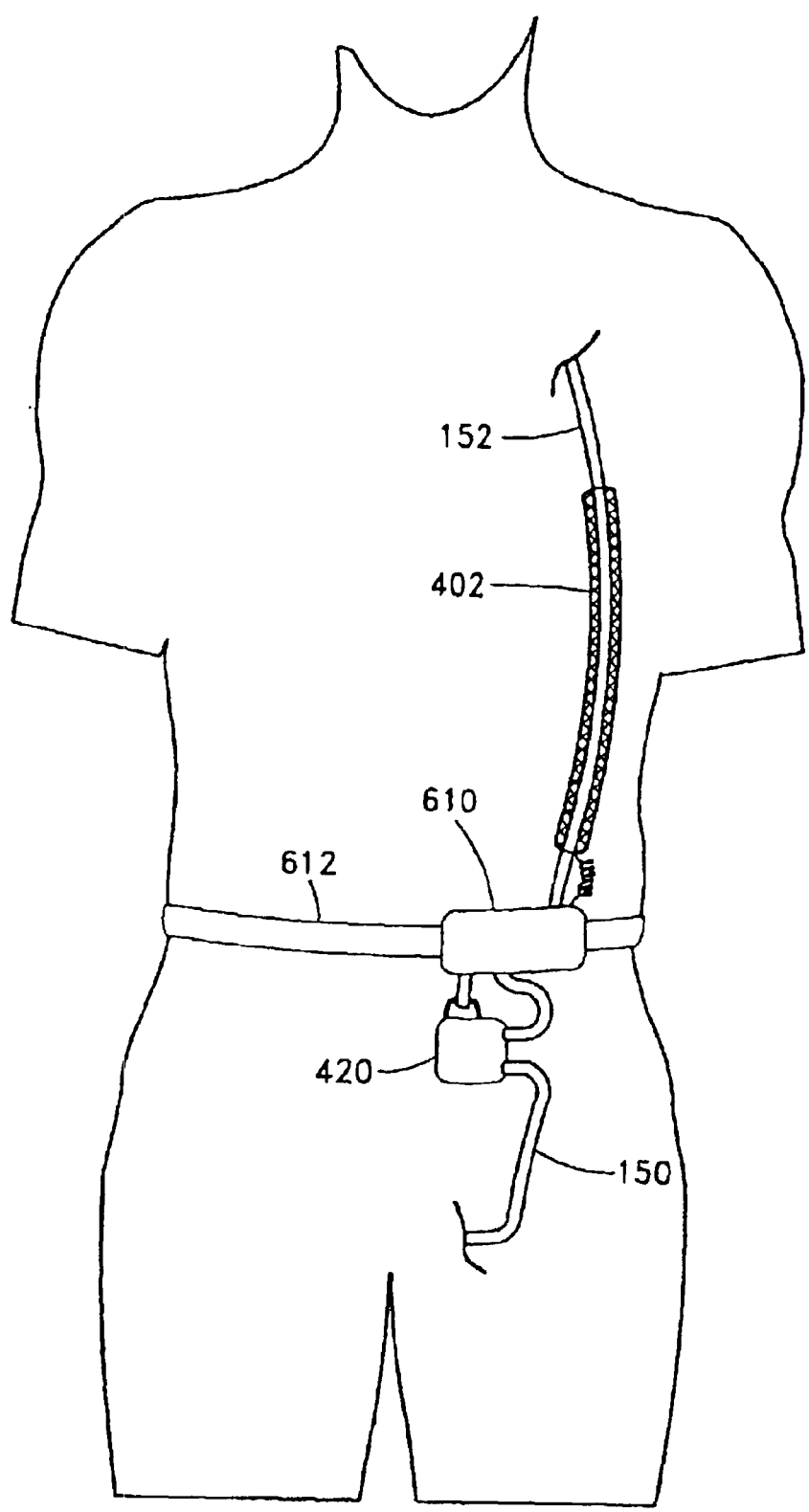
FIG. 9 is a schematic view of a sixth embodiment of the present invention showing a reservoir and a portable housing for carrying a portion of the invention directly on the patient.

It is contemplated that a means for minimizing the loss of thermal energy in the patient's blood be provided where the present inventive system is applied extracorporeally. Such means for minimizing the loss of thermal energy may comprise, for example, a heated bath through which the inflow and outflow conduits pass or, alternatively, thermal elements secured to the exterior of the inflow and outflow conduits. Referring to FIG. 9, one embodiment comprises an insulating wrap 402 surrounding the outflow conduit 152 having one or more thermal elements passing therethrough. The elements may be powered, for example, by a battery (not shown). One advantage of thermal elements is that the patient may be ambulatory, if desired. Other means that are known by persons of ordinary skill in the art for ensuring that the temperature of the patient's blood remains at acceptable levels while travelling extracorporeally are also contemplated.

An alternative variation of the third embodiment may be used where it is desired to treat a patient periodically, but for short periods of time each occasion and without the use of special connectors. With this variation, it is contemplated that the second ends of the inflow and outflow conduits be more permanently connected to the associated blood vessels via, for example, an anastomosis connection, wherein a portion of each conduit proximate to the blood vessel connection is implanted percutaneously with a removable cap enclosing the externally-exposed first end (or an intervening end thereof) of the conduit external to the patient. When it is desired to provide a circulatory flow path to supplement blood flow, the removable cap on each exposed percutaneously-positioned conduit could be removed and the pump (or the pump with a length of inflow and/or outflow conduit attached thereto) inserted between the exposed percutaneous conduits. In this regard, a patient may experience the benefit of the present invention periodically, without having to reconnect and redisconnect the conduits from the blood vessels each time.

Figure 6:
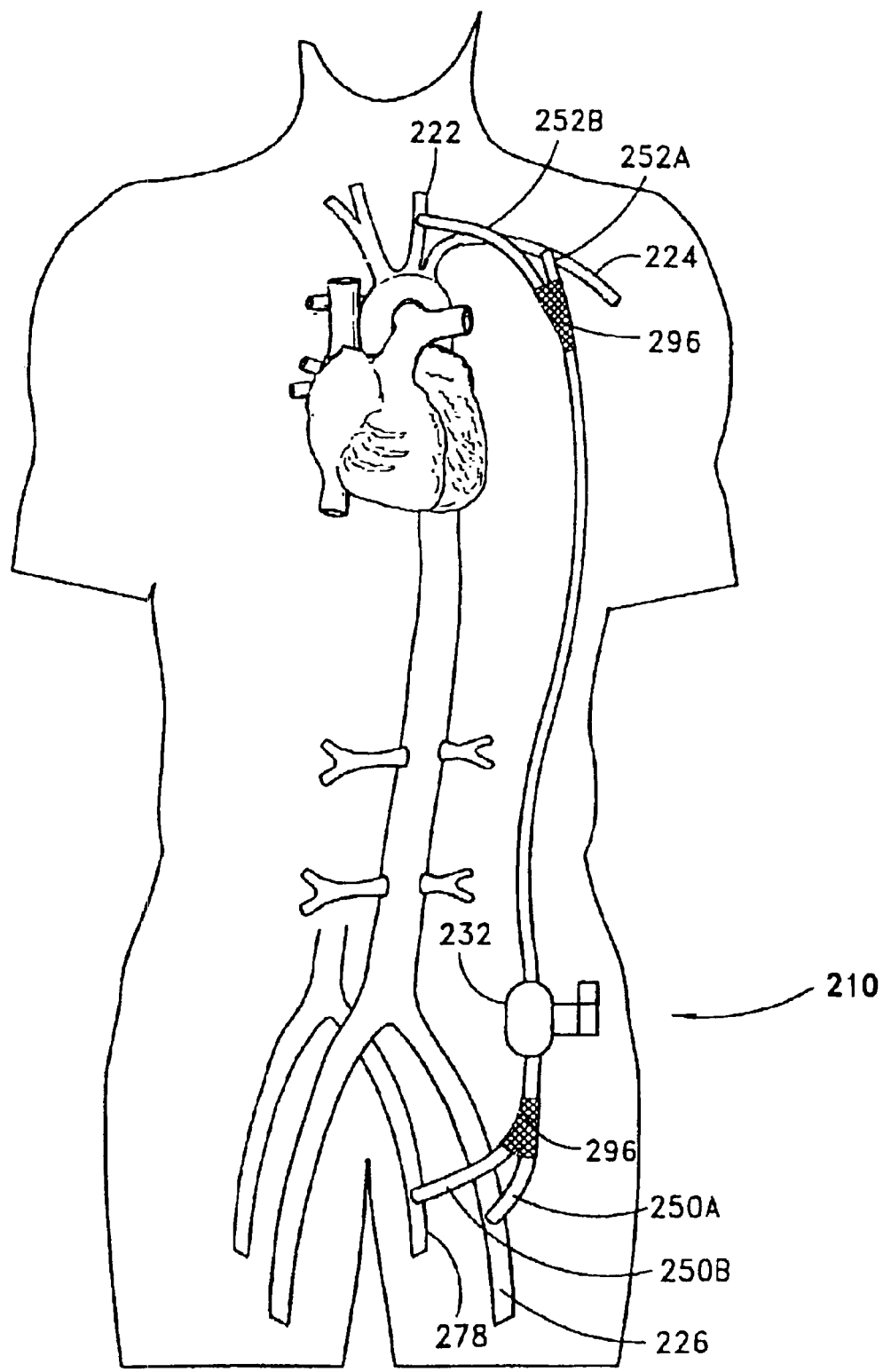
FIG. 6 is a schematic view of a fourth embodiment of the present invention, shown applied to a patient's circulatory system.

Another embodiment of the present invention includes a plurality of inflow and/or outflow conduits. For example, with reference to FIG. 6, a fourth embodiment of the present invention 210 includes a pump 232 in fluid communication with a plurality of inflow conduits 250A, 250B and a plurality of outflow conduits 252A, 252B. Each pair of conduits converges at a generally Y-shaped convergence 296 that converges the flow at the inflow end and diverges the flow at the outflow end. Each conduit may be connected to a separate peripheral blood vessel, although it is possible to have two connections to the same blood vessel at remote locations. In one arrangement, all four conduits are connected to peripheral arteries. Alternatively, one or more of the conduits could be connected to veins. In the application shown in FIG. 6, inflow conduit 250A is connected to left femoral artery 226 while inflow conduit 250B is connected to left femoral vein 278. Outflow conduit 252A is connected to left axillary artery 224 while outflow conduit 252B is connected to left carotid artery 222. It should be noted that the connections of any or all of the conduits to the blood vessels may be via an anastomosis connection or via a special connector, as described above. In addition, the embodiment of FIG. 6 may be applied to any combination of peripheral blood vessels that would best suit the patient's condition. For example, it may be desired to have one inflow conduit and two outflow conduits or vice versa. It should be noted that more than two conduits may be used on the inflow or outflow side, where the number of inflow conduits is not necessarily equal to the number of outflow conduits.

If desired, the present inventive system may further comprise a reservoir that is either contained within or in fluid communication with the inflow conduit. This reservoir is preferably made of materials that are nonthrombogenic. Referring to FIG. 9, a reservoir 420 is positioned fluidly in line with the inflow conduit 150. The reservoir 420 serves to sustain adequate blood in the system when the pump demand exceeds momentarily the volume of blood available in the peripheral blood vessel in which the inflow conduit resides until the pump output can be adjusted. The reservoir reduces the risk of excessive drainage of blood from the peripheral blood vessel, which may occur when cardiac output falls farther than the already diminished baseline level of cardiac output, or when there is systemic vasodilation, as can occur, for example, with septic shock. It is contemplated that the reservoir would be primed with an acceptable solution, such as saline, when the present system is first applied to the patient.

Figure 8:
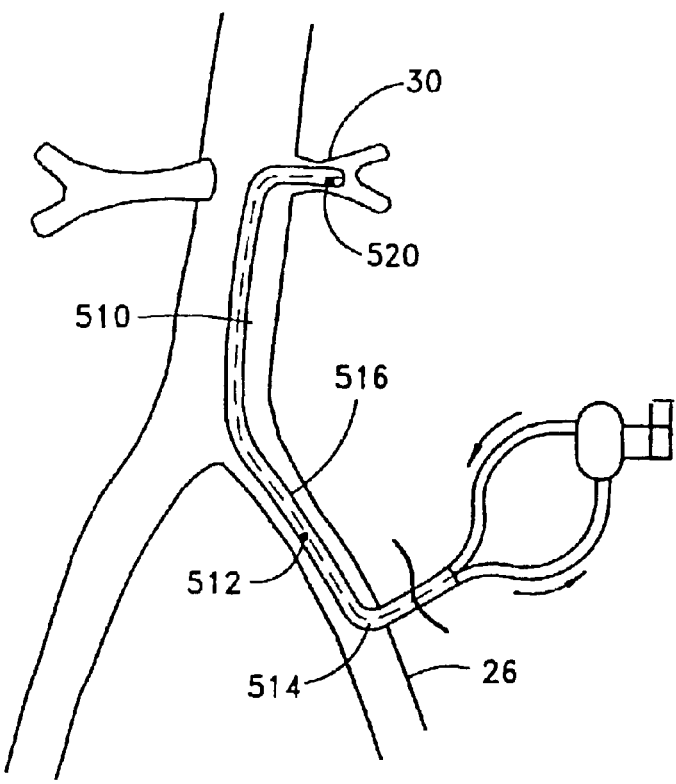
FIG. 8 is a schematic view of a fifth embodiment of the present invention employing a multi-lumen catheter for single site application to a patient.

In an alternative embodiment, the present system comprises a multi-lumen catheter whereby the system may be applied by insertion at a single cannulated site while the inflow and outflow conduits still fluidly communicate with peripheral vessels. Referring to FIG. 8, a multi-lumen catheter 510 could be inserted, for example, into the left femoral artery 26 and guided superiorly through the descending aorta to one of numerous locations. The blood could discharge, for example, directly into the descending aorta proximate an arterial branch, such as the left subclavian artery or, as shown in FIG. 2 by way of example, directly into the peripheral mesenteric artery 30. Preferably, the multi-lumen catheter 510 has an inflow port 512 that may be positioned within the left femoral artery 26 when the catheter 510 is fully inserted so that blood drawn from the left femoral artery is directed through the inflow port 512 into a first lumen 514 in the catheter. This blood is then pumped through a second lumen 516 in the catheter and out through an outflow port 520 at the distal end of the catheter 510. The outflow port 520 may be situated within, for example, the mesenteric artery 30 such that blood flow results from the left femoral artery 26 to the mesenteric artery 30. Preferably, where there is a desire for the patient to be ambulatory, the multi-lumen catheter 510 should preferably be made of material sufficiently flexible and resilient to permit the patient to be comfortably move about while the catheter is indwelling in the patient's blood vessels without causing any vascular trauma.

As explained above for several embodiments, one of the advantages of the present heart assist system is that it permits the patient to be ambulatory. If desired, the system may be designed portably so that it may be carried directly on the patient. Referring to FIG. 9, this may be accomplished through the use of a portable case 610 with a belt strap 612 to house the pump, power supply and/or the controller, along with certain portions of the inflow and/or outflow conduits, if necessary. It may also be accomplished with a shoulder strap or other techniques, such as a backpack or a fanny pack, that permit effective portability. As shown in FIG. 9, blood is drawn through the inflow conduit 150 into a pump contained within the portable case 610, where it is discharged into the outflow conduit 152 back into the patient.

Figure 12:
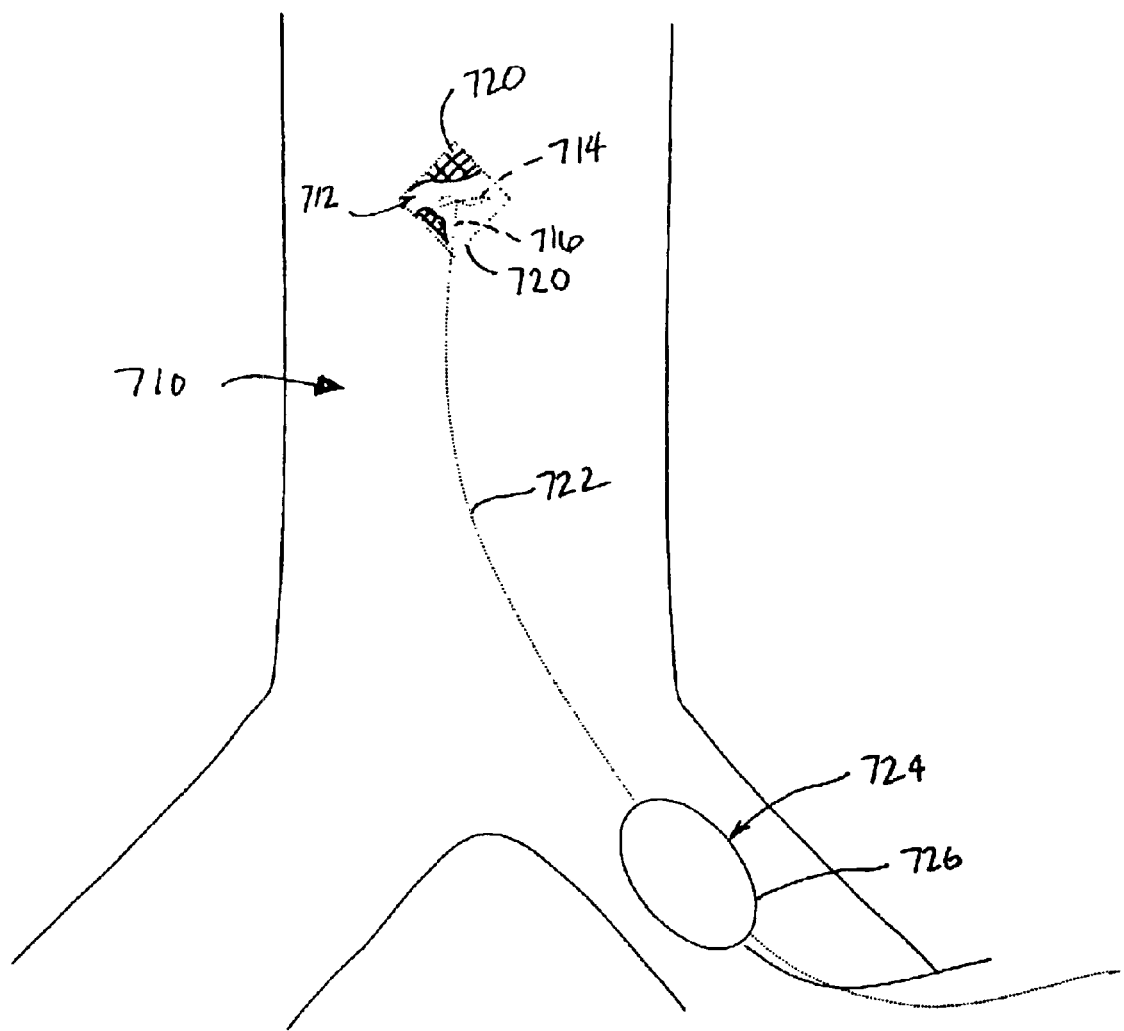
FIG. 12 is a schematic view of a seventh embodiment of the present invention employing an intravascular pump inserted through a non-primary vessel in which the pump is enclosed in a protective housing without inflow and outflow conduits.

An alternative embodiment of the present invention takes further advantage of the supplemental blood perfusion and heart load reduction benefits while remaining minimally invasive in application. Specifically, it is contemplated to provide an extracardiac pumping system that comprises a pump that is sized and configured to be implanted intravascularly in any location desirable to achieve those benefits, while being insertable through a non-primary vessel. Referring to FIG. 12, one intravascular embodiment 710 of the present invention is intended for use within a patient's vasculature, as shown, and comprises a pumping means 712 comprising preferably one or more rotatable impeller blades 714, although other types of pumping means are contemplated, such as an archimedes screw, a worm pump, or other means by which blood may be directed axially along the pumping means from a point upstream of an inlet to the pumping means to a point downstream of an outlet from the pumping means. Where one or more impellers are used, such as a rotary pump, such impellers may be supported helically or otherwise on a shaft 716 within a housing 720. The housing 720 may be open, as shown, in which the walls of the housing are open to blood flow therethrough. The housing, if desired, may be entirely closed except for an inlet and outlet (not shown) to permit blood flow therethrough in a more channel fashion. In either case, the invention serves to supplement the kinetic energy of the blood flow through the blood vessel in which the pump is positioned.

The pump impeller blade(s) 714 of this embodiment may be driven in one or a number of ways known to persons of ordinary skill in the art. In the embodiment shown in FIG. 12, the pump impeller is driven mechanically via a rotatable cable or drive wire 722 by driving means 724, the latter of which may be positioned corporeally (within or without the vasculature) or extracorporeally. As shown, the driving means 724 may comprise a motor 726 to which energy is supplied directly via an associated battery or an external power source, in a manner described in more detail herein. It is also contemplated that the pump be driven electromagnetically through an internal or external electromagnetic drive. Preferably, a controller (not shown) is provided in association with this embodiment so that the pump may be controlled to operate in a continuous and/or pulsatile fashion, as described herein.

Figure 13:
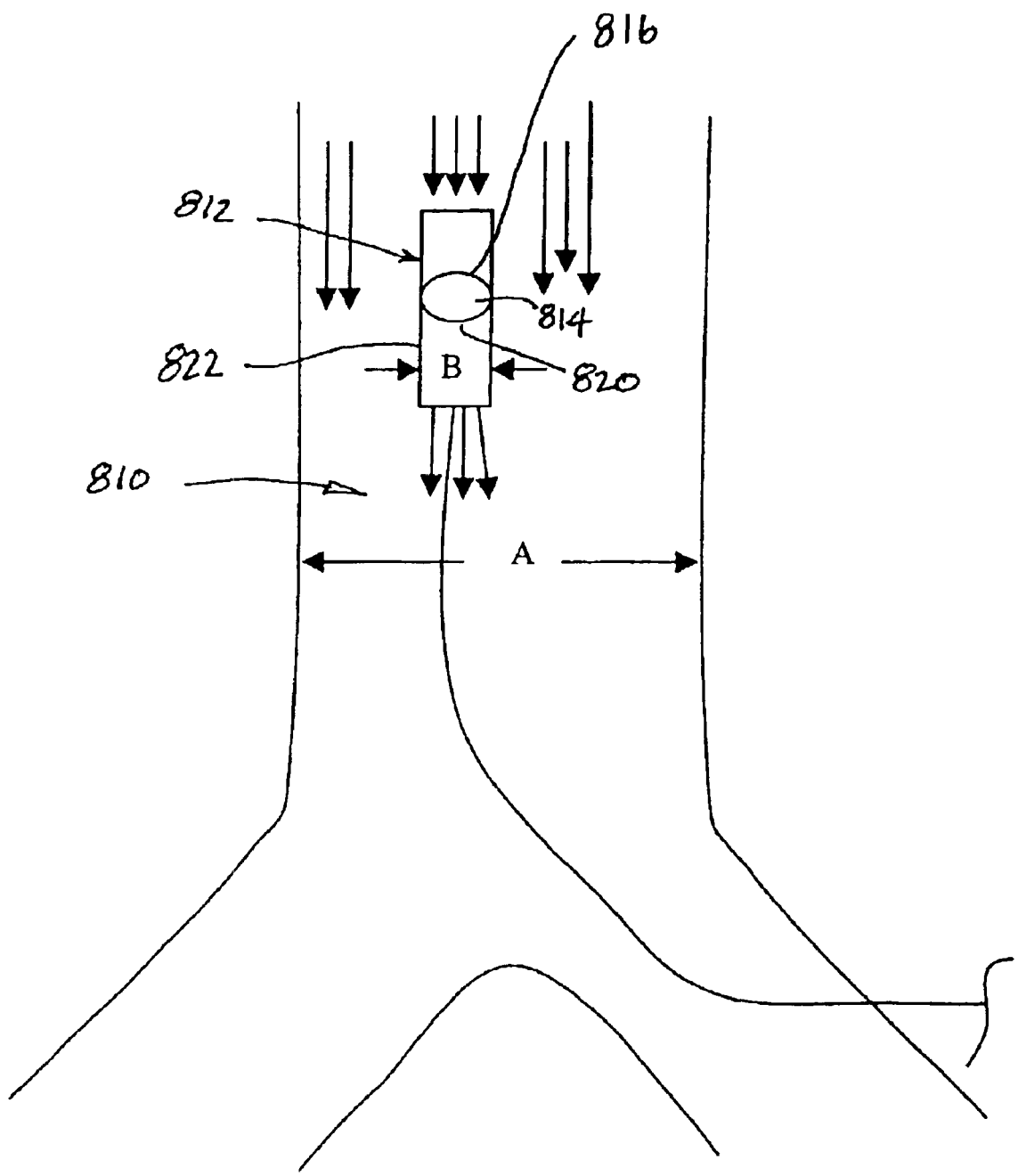
FIG. 13 is a schematic view of an eighth embodiment of the present invention employing an intravascular pump inserted through a non-primary vessel in which the pump is housed within a conduit having an inlet and an outlet.
Figure 14:
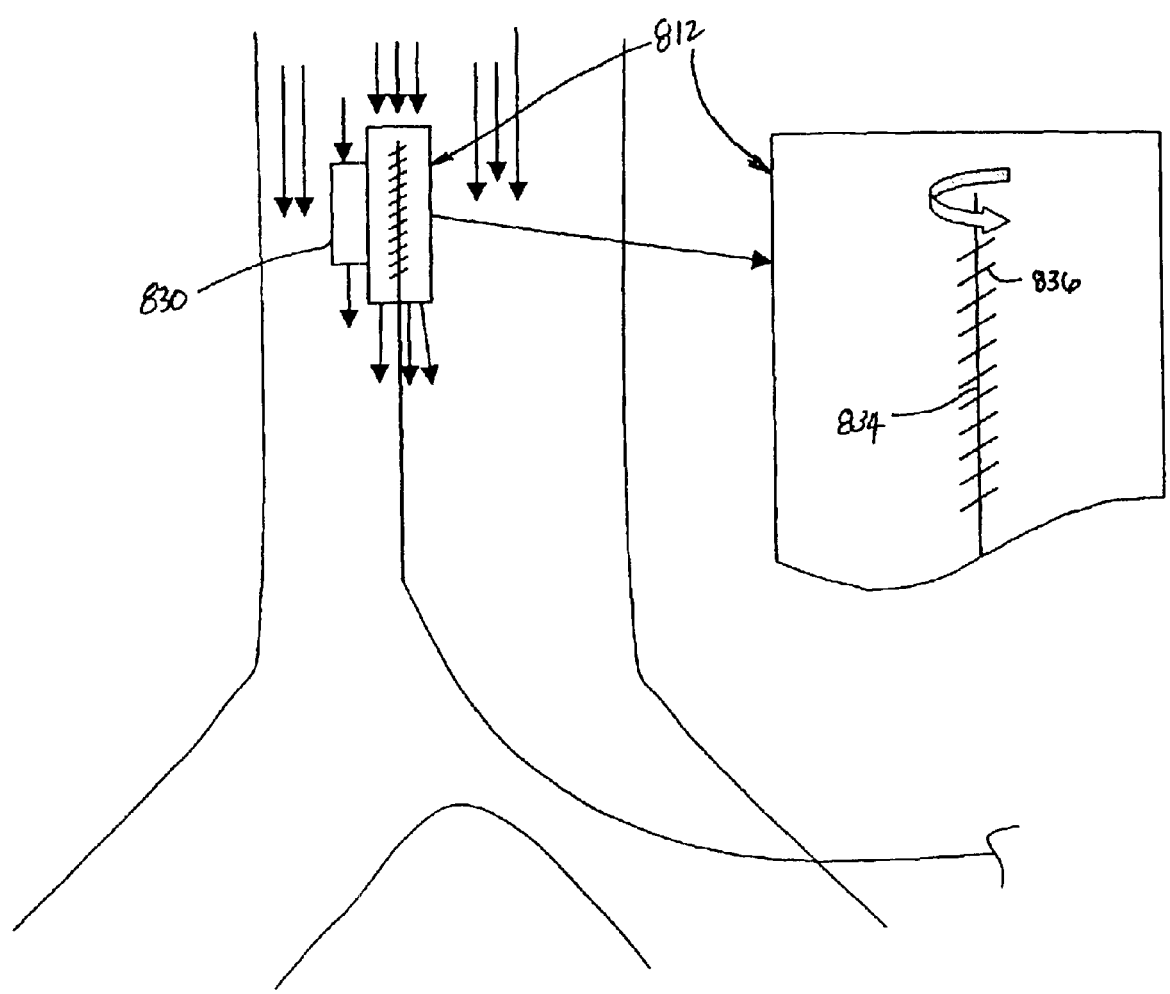
FIG. 14 is a schematic view of a variation of the eighth embodiment of FIG. 13 in which an additional conduit is shown adjacent the conduit housing the pump, and in which the pump comprises a shaft mounted helical thread.

Variations of the intravascular embodiment of FIG. 12 are shown in FIGS. 13 and 14. In the embodiment of FIG. 13, the present invention consists of an intravascular extracardiac system 810 comprising a pumping means 812, which may be one of several means described herein, whereby the pump means may be driven by one of several pumping means described herein, including means that is sized and configured to be implantable and, if desired, implantable intravascularly. For a blood vessel (e.g., descending aorta) having a diameter "A", the pumping means preferably has a meaningfully smaller diameter "B". The pumping means 812 may comprise a pump 814 having an inlet 816 and outlet 820 housed within a conduit 822, or may comprise a pump and inflow and outflow conduits (not shown) fluidly connected to the inlet and outlets of pump 814, respectively. The conduit 822 may be relatively short, as shown, or may extend well within the designated blood vessel or even into an adjoining or remote blood vessel at either the inlet end, the outlet end, or both. In an alternative embodiment, an intrasvascular pumping means may be positioned within one lumen of a multilumen catheter so that, for example, where the catheter is applied at the left femoral artery, a first lumen may extend into the aorta proximate the left subclavian and the pumping means may reside at any point within the first lumen, and the second lumen may extend much shorter just into the left femoral or left iliac.

In the case of the pumping means of FIG. 13, the means comprises a rotary pump driven mechanically by a drive. Referring to FIG. 14, the intravascular extracardiac system may further comprise an additional conduit 830 positioned preferably proximate the pumping means 812 to provide a defined flow path for blood flow axially parallel to the blood flowing through the pumping means. In the case of the pumping means of FIG. 14, the means comprises a rotatable cable 834 having blood directing means 836 supported therein for directing blood axially along the cable. Other types of pumping means are also contemplated, if desired, for use with the additional conduit 830.

The intravascular extracardiac system described herein may be inserted into a patient's vasculature in any means known by one of ordinary skill or obvious variant thereof. In one method of use, the system is temporarily housed within a catheter that is inserted percutaneously, or by surgical cutdown, into a non-primary blood vessel and fed through to a desired location. The catheter may be withdrawn away from the system so as not to interfere with operation of the system, but still permit the withdrawal of the system from the patient when desired.

Figure 15:
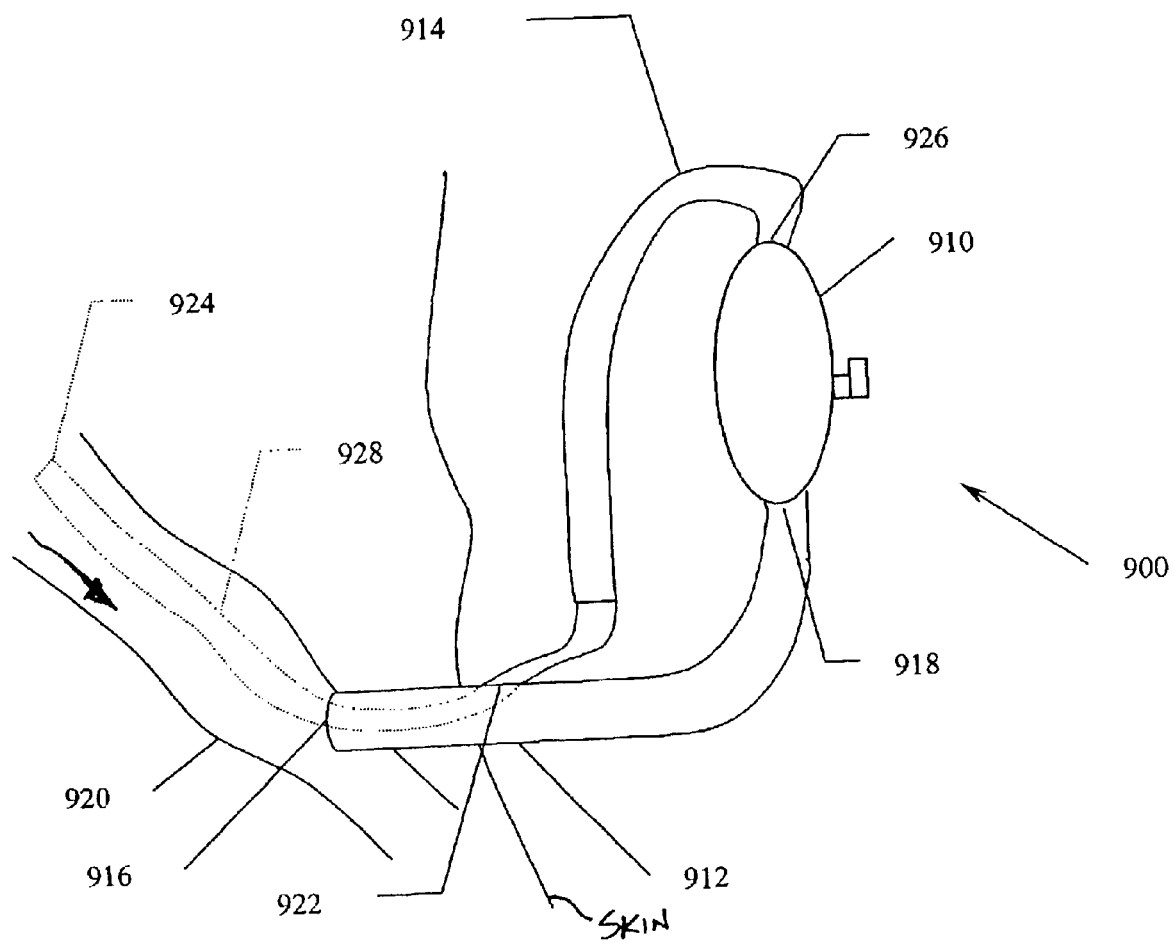
FIG. 15 is a schematic view of a ninth embodiment of the present invention employing an inflow vascular graft conduit coupled to a non-primary blood vessel and to a pump, and an outflow conduit fluidly coupled to a blood vessel through the inflow conduit.

Another alternative embodiment of the present invention takes further advantage of the supplemental blood perfusion and heart load reduction benefits while remaining minimally invasive in application. Referring to FIG. 15, an extracardiac pumping system 900 comprises a pump 910, an inflow conduit comprising a vascular graft 912, and an outflow conduit 914, wherein each of the vascular graft conduit 912 and the outflow conduit 914 are fluidly coupled to pump 910. The pump 910 is configured to pump blood through the patient at subcardiac volumetric rates, and has an average flow rate that, during normal operation thereof, is substantially below that of the patient's heart when healthy. In one variation, the pump 910 may be a rotary pump. Other pumps described herein, or any other suitable pump can also be used in the extracardiac pumping system 900. In one application, the pump 910 is configured so as to be implantable.

The vascular graft 912 has a first distal end 916 and a second proximal end 918. The first end 916 is sized and configured to couple to a non-primary blood vessel 920 subcutaneously to permit application of the extracardiac pumping system 900 in a minimally-invasive procedure. In one application, the vascular graft conduit is configured to couple to the blood vessel via an anastomosis connection. The second end 918 of the vascular graft 912 is fluidly coupled to the pump 910 to conduct blood between the non-primary blood vessel 920 and the pump 910. In the embodiment shown, the second end 918 is directly connected to the pump 910, but, as discussed above in connection with other embodiments, intervening fluid conducting elements may be interposed between the second end 918 of the vascular graft 912 and the pump 910. Examples of arrangements of vascular graft conduits may be found in U.S. application Ser. No. 09/780,083, filed Feb. 9, 2001, entitled EXTRA-CORPOREAL VASCULAR CONDUIT, which is hereby incorporated by reference in its entirety and made a part of this specification.

FIG. 15 illustrates that the present inventive embodiment further comprises means for connecting the outflow conduit to the vascular graft 912, which may comprise in one embodiment an insertion site 922. In the illustrated embodiment, the insertion site is located between the first end 916 and the second end 918 of the vascular graft 912. The insertion site 922 is configured to receive the outflow conduit 914 therethrough in a sealable manner. The outflow conduit 914 has a first distal end 924 sized and configured as a cannula 928 to be inserted through the non-primary blood vessel 920 through the vascular graft 912. The conduit has a second proximal end 926 fluidly coupled to the pump 910 to conduct blood between the pump 910 and the patient.

The extracardiac pumping system 900 can be applied to a patient, as shown in FIG. 15, so that the outflow conduit 914 provides fluid communication between the pump 910 and a location upstream or downstream of the point where the cannula 928 of the outflow conduit enters the non-primary blood vessel 920. In another application, the cannula 928 is directed through the blood vessel to a different blood vessel, upstream or downstream thereof. Although the vascular graft 912 is described above as an "inflow conduit" and the conduit 914 is described above as an "outflow conduit," in another aspect of this embodiment, the blood flow through the pumping system 900 is reversed (i.e., the pump 910 pumps blood in the opposite direction), whereby the vascular graft 912 is an outflow conduit and the conduit 914 is an inflow conduit.

Figure 16:
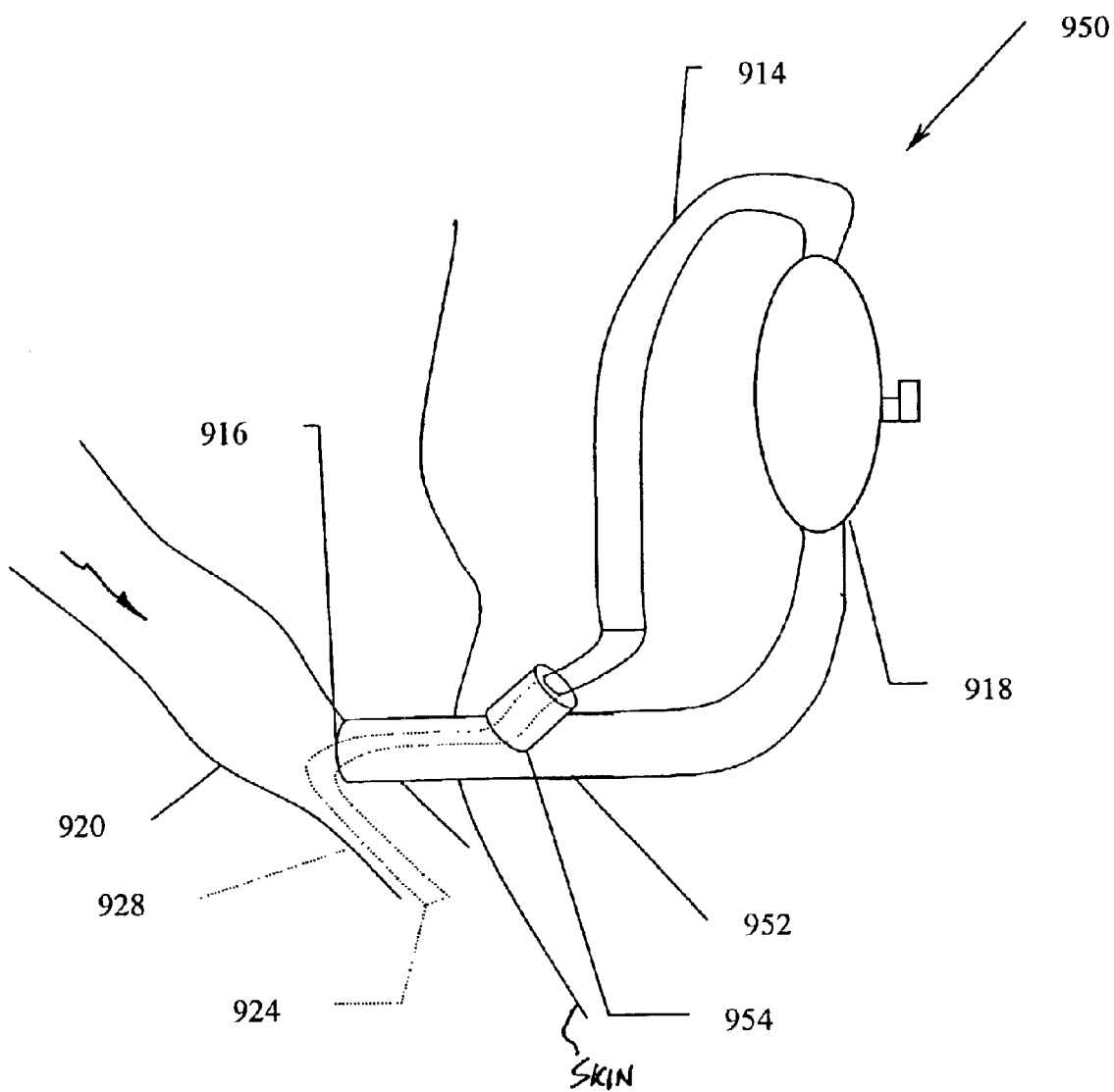
FIG. 16 is a schematic view of a variation of the ninth embodiment of the present invention.

A variation of the extracardiac pumping system in FIG. 15 is shown in FIG. 16. Extracardiac pumping system 950 is similar to the extracardiac pumping system 900 and includes a vascular graft 952 that comprises the first end 916, the second end 918, and means for connecting the outflow conduit 914 to the vascular graft 952. The means for connecting the conduit 914 to the vascular graft 952 may comprise a branched portion 954. In one embodiment, the branched portion 954 is located between the first end 916 and the second end 918. The branched portion 954 is configured to sealably receive the distal end of outflow conduit 914. Where, as shown, the first end 924 of the outflow conduit 914 comprises the cannula 928, the branched portion 954 is configured to receive the cannula 928. The inflow conduit 952 of this arrangement comprises in part a multi-lumen catheter, where the internal lumen extends into the blood vessel 920. Examples of such an arrangement of a multi-lumen catheter are shown in U.S. application Ser. No. 10/078,283, filed Feb. 14, 2002, entitled A MULTILUMEN CATHETER FOR MINIMIZING LIMB ISCHEMIA, which is hereby incorporated by reference in its entirety and made a part of this specification.

An important advantage of the present invention is its potential to enhance mixing of systemic arterial blood, particularly in the aorta. Such enhanced mixing ensures the delivery of blood with higher oxygen-carrying capacity to organs supplied by arterial side branches off of the aorta. A method of enhancing mixing utilizing the present invention preferably includes taking steps to assess certain parameters of the patient and then to determine the minimum output of the pump that, when combined with the heart output, ensures turbulent flow in the aorta, thereby enhancing blood mixing.

Blood flow in the aortic arch during normal cardiac output may be characterized as turbulent in the end systolic phase. It is known that turbulence in a flow of fluid through pipes and vessels enhances the uniform distribution of particles within the fluid. It is believed that turbulence in the descending aorta enhances the homogeneity of blood cell distribution in the aorta. It is also known that laminar flow of viscous fluids leads to a higher concentration of particulates in the central portion of pipes and vessels through which the fluid flows. It is believed that, in low flow states such as that experienced during heart failure, there is reduced or inadequate mixing of blood cells leading to a lower concentration of nutrients at the branches of the aorta to peripheral organs and tissues. As a result, the blood flowing into branch arteries off of the aorta will likely have a lower hematocrit, especially that flowing into the renal arteries, the celiac trunk, the spinal arteries, and the superior and inferior mesenteric arteries. That is because these branches draw from the periphery of the aorta The net effect of this phenomenon is that the blood flowing into these branch arteries has a lower oxygen-carrying capacity, because oxygen-carrying capacity is directly proportional to both hematocrit and the fractional $O_2$ saturation of hemoglobin. Under those circumstances, it is very possible that these organs will experience ischemia-related pathology.

The phenomenon of blood streaming in the aorta, and the resultant inadequate mixing of blood resulting in central lumenal concentration of blood cells, is believed to occur when the Reynolds number ($N_R$) for the blood flow in the aorta is below 2300. To help ensure that adequate mixing of blood will occur in the aorta to prevent blood cells from concentrating in the center of the lumen, a method of applying the present invention to a patient may also include steps to adjust the output of the pump to attain turbulent flow within the descending aorta upstream of the organ branches; i.e., flow exhibiting a peak Reynolds number of at least 2300 within a complete cycle of systole and diastole. Because flow through a patient is pulsatile in nature, and not continuous, consideration must be given to how frequently the blood flow through the aorta has reached a certain desired velocity and, thus, a desired Reynolds number. The method contemplated herein, therefore, should also include the step of calculating the average Womersley number ($N_W$), which is a function of the frequency of the patient's heart beat. It is desired that a peak Reynolds number of at least 2300 is attained when the corresponding Womersley number for the same blood flow is approximately 6 or above.

More specifically, the method may comprise calculating the Reynolds number for the blood flow in the descending aorta by determining the blood vessel diameter and both the velocity and viscosity of the fluid flowing through the aorta. The Reynolds number may be calculated pursuant to the following equation:

$$N_R = \frac{V \cdot d}{\upsilon}$$

where: V=the velocity of the fluid; d=the diameter of the vessel; and $\upsilon$=the viscosity of the fluid. The velocity of the blood flowing through the aorta is a function of the cross-sectional area of the aorta and the volume of flow therethrough, the latter of which is contributed both by the patient's own cardiac output and by the output of the pump of the present invention. Velocity may be calculated by the following equation:

$$N_W = r\sqrt{\frac{2\pi\omega}{\upsilon}}$$

where Q=the volume of blood flowing through the blood vessel per unit time, e.g., the aorta, and r=radius of the aorta. If the relationship between the pump output and the velocity is already known or independently determinable, the volume of blood flow Q may consist only of the patient's cardiac output, with the knowledge that that output will be supplemented by the subcardiac pump that is part of the present invention. If desired, however, the present system can be implemented and applied to the patient first, before calculating Q, which would consist of the combination of cardiac output and the pump output.

The Womersley number may be calculated as follows:

$$V = \frac{Q}{\pi r^2}$$

where r is the radius of the vessel being assessed, $\omega$ is the frequency of the patient's hearbeat, and $\upsilon$=the viscosity of the fluid. For a peak Reynolds number of at least 2300, a Womersley number of at least 6 is preferred, although a value as low as 5 would be acceptable.

By determining (i) the viscosity of the patient's blood, which is normally about 3.0 $mm^2$/sec (kinematic viscosity), (ii) the cardiac output of the patient, which of course varies depending upon the level of CHF, and (iii) the diameter of the patient's descending aorta, which varies from patient to patient but is about 21 mm for an average adult, one can determine the flow rate Q that would result in a velocity through the aorta necessary to attain a Reynolds number of at least 2300 at its peak during the patient's heart cycle. Based upon that determination of Q, one may adjust the output of the pump of the present invention to attain the desired turbulent flow characteristic through the aorta, enhancing mixing of the blood therethrough.

One may use ultrasound (e. g., echocardiography or abdominal ultrasound) to measure the diameter of the aorta, which is relatively uniform in diameter from its root to the abdominal portion of the descending aorta. Furthermore, one may measure cardiac output using a thermodilution catheter or other techniques known to those of skill in the art. Finally, one may measure viscosity of the patient's blood by using known methods; for example, using a capillary viscosimeter. It is expected that in many cases, the application of this embodiment of the present method will provide a basis to more finely tune the system to more optimally operate the system to the patient's benefit. Other methods contemplated by the present invention may include steps to assess other patient parameters that enable a person of ordinary skill in the art to optimize the present system to ensure adequate mixing within the vascular system of the patient.

Alternative inventive methods that provide the benefits discussed herein include the steps of, prior to applying a shape change therapy, applying a blood supplementation system (such as one of the many examples described herein) to a patient, whereby the methods are designed to improve the ability to reduce the size and/or wall stress of the left ventricle, or both ventricles, thus reducing ventricular loading. Specifically, one example of such a method comprises the steps of providing a pump configured to pump blood at subcardiac rates, providing inflow and outflow conduits configured to fluidly communicate with non-primary blood vessels, fluidly coupling the inflow conduit to a non-primary blood vessel, fluidly coupling the outflow conduit to the same or different (primary or non-primary) blood vessel and operating the subcardiac pump in a manner, as described herein, to reduce the load on the heart, wherein the fluidly coupling steps may comprises anastomosis, percutaneous cannulazation, positioning the distal end of one or both conduits within the desired terminal blood vessel or any combination thereof. The method further comprises, after sufficient reduction in ventricular loading, applying a shape change therapy in the form of, for example, a cardiac reshaping device, such as those referred to herein, or others serving the same or similar function, for the purpose of further reducing the size of and/or wall stress on one or more ventricles and, thus, the heart, and/or for the purpose of maintaining the patient's heart at a size sufficient to enhance recovery of the patient's heart.

While the above description has explained the inventive features of the invention as applied to various embodiments, it will be understood that the variations in the form and details of the apparatus or method may be made by those of ordinary skill in the art without departing from the spirit of the invention. The scope of the invention is indicated by the appended claims herein, however, not by the foregoing description.

What is claimed is:

1. An extracardiac pumping system for supplementing blood circulation through a patient without any component thereof being connected to the patient's heart, the extracardiac system comprising:

a pump configured to pump blood through the patient at subcardiac volumetric rates, said pump having an average flow rate that, during normal operation thereof, is substantially below that of the patient's heart when healthy;

a first conduit comprising at least in part biocompatible synthetic material having a first distal end sized and configured to fluidly couple to a non-primary blood vessel, the first conduit also being fluidly coupled to the pump to conduct blood between the pump and the non-primary blood vessel; and a second conduit having a first distal end sized and configured to be positioned at least in part within the non-primary blood vessel and within the first conduit, the second conduit being fluidly coupled to the pump to conduct blood between the pump and the patient, the first conduit further comprising means for permitting the second conduit to sealably extend through a wall of said first conduit to form an internal lumen within the proximal end of the first conduit;

whereby the first conduit may be fluidly coupled to the blood vessel subcutaneously to permit application of the extracardiac pumping system in a minimally-invasive procedure through a single site and whereby the second conduit may extend into the non-primary blood vessel so that the distal end of said second conduit may reside either in said blood vessel or a different blood vessel.

2. The extracardiac pumping system of claim 1, wherein the first conduit is configured as an inflow conduit and the second conduit is configured as an outflow conduit.

3. The extracardiac pumping system of claim 1, wherein the first conduit is configured an outflow conduit and the second conduit is configured as an inflow conduit.

4. The extracardiac pumping system of claim 1, wherein the means for permitting the second conduit to sealably extend through a wall of said first conduit comprises an insertion site in said first conduit wall sized to tightly fit over the exterior wall of the second conduit extending therethrough and configured to permit a reliable seal between the first conduit wall and the exterior of the second conduit.

5. The extracardiac pumping system of claim 1, further comprising a branched portion on the first conduit located between the first and second end of said first conduit, the insertion site being positioned on said branched portion.

6. The extracardiac pumping system of claim 1, wherein the means for permitting the second conduit to sealably extend through a wall of said first conduit comprises a connector extending from said first conduit configured to sealably connect to a distal end of said second conduit; the first conduit further comprising an internal lumen in sealed fluid communication with said connector to permit fluid communication between the second conduit and the internal lumen when the distal end of the second conduit is connected to the connector without said fluid residing in said second conduit significantly leaking into the first conduit.

7. The extracardiac pumping system of claim 1, wherein the pump is a rotary pump.

8. The extracardiac pumping system of claim 1, wherein the pump is implantable.

9. The extracardiac pumping system of claim 1, wherein the system is implantable.

10. The extracardiac pumping system of claim 1, wherein the first conduit is configured to couple to the blood vessel via an anastomosis procedure.

11. A method for supplementing the circulation of blood through a patient without connecting any component to the patient's heart, the method comprising the steps of:

connecting a first end of a first conduit to a non-primary blood vessel using a minimally invasive procedure to permit the flow of blood between a pump and the non-primary blood vessel, the pump configured to pump blood at volumetric rates that are on average subcardiac;

fluidly coupling a distal end of a second conduit, which is fluidly coupled to the pump at a proximal end, to the patient's vasculature through the first conduit and through at least a part of the non-primary blood vessel so that the distal end of said second conduit resides within the same or different blood vessel; and operating the pump to perfuse blood through the patient's circulatory system at volumetric rates that are on average subcardiac between the non-primary blood vessel and the same or different blood vessel.

12. The method of claim 11, wherein the step of fluidly coupling a distal end of the second conduit to the patient's vasculature comprises directing the distal end of the second conduit through an insertion site positioned on said first conduit.

13. The method of claim 11, wherein the step of fluidly coupling a distal end of the second conduit to the patient's vasculature comprises connecting the distal end of the second conduit to a connector extending from said first conduit.

14. The extracardiac pumping system of claim 11, wherein the first conduit is configured to couple to the blood vessel via an anastomosis procedure.

\* \* \* \* \*